(12) United States Patent
Sainz et al.

(10) Patent No.: US 9,434,953 B2
(45) Date of Patent: Sep. 6, 2016

(54) METHODS AND COMPOSITIONS FOR MODIFIED ETHANOL INDUCIBLE PROMOTER SYSTEMS

(75) Inventors: Manuel Benito Sainz, Ribeirão Preto (BR); Mark David Kinkema, Brisbane (AU)

(73) Assignees: SYNGENTA PARTICIPATIONS AG, Basel (CH); QUEENSLAND UNIVERSITY OF TECHNOLOGY, Brisbane (AU)

( * ) Notice: Subject to any disclaimer, the term of this patent is extended or adjusted under 35 U.S.C. 154(b) by 293 days.

(21) Appl. No.: 13/978,133

(22) PCT Filed: Dec. 15, 2011

(86) PCT No.: PCT/US2011/065184
§ 371 (c)(1),
(2), (4) Date: Jul. 15, 2013

(87) PCT Pub. No.: WO2012/099664
PCT Pub. Date: Jul. 26, 2012

(65) Prior Publication Data
US 2013/0291233 A1 Oct. 31, 2013

Related U.S. Application Data

(60) Provisional application No. 61/433,658, filed on Jan. 18, 2011.

(51) Int. Cl.
*C12N 15/113* (2010.01)
*C12N 15/82* (2006.01)
(52) U.S. Cl.
CPC ......... *C12N 15/8238* (2013.01); *C12N 15/113* (2013.01); *C12N 15/8241* (2013.01)

(58) Field of Classification Search
None
See application file for complete search history.

(56) References Cited

U.S. PATENT DOCUMENTS

| 4,808,537 A | 2/1989 | Stroman et al. |
| 6,605,754 B1 | 8/2003 | Caddick et al. |

(Continued)

FOREIGN PATENT DOCUMENTS

| GB | 2374598 A | 10/2002 |
| KR | 2005-0022491 A | 3/2005 |

(Continued)

OTHER PUBLICATIONS

Espley et al. Multiple repeats of a promoter segment causes transcription factor autoregulation in red apples. The Plant Cell. 2009. 21: 168-183.*

(Continued)

*Primary Examiner* — Shubo (Joe) Zhou
*Assistant Examiner* — Ashley K Buran
(74) *Attorney, Agent, or Firm* — Myers Bigel & Sibley, P.A.

(57) ABSTRACT

The present invention provides nucleic acid molecules comprising one or more nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10 that can be operably linked to a promoter, thereby making the promoter inducible by a chemical compound that can induce the expression of the alcohol dehydrogenase system of *Aspergillus nidulans*. Methods for making an inducible promoter and for making the expression of a nucleotide sequence of interest inducible are also provided. Further provided are plants, plant parts, and plant cells, comprising the compositions of the present invention.

11 Claims, 5 Drawing Sheets

(56) References Cited

U.S. PATENT DOCUMENTS

| | | | |
|---|---|---|---|
| 7,112,723 | B2 | 9/2006 | Streatfield et al. |
| 2004/0154051 | A1 | 8/2004 | Cade et al. |
| 2004/0157287 | A1* | 8/2004 | Greenland et al. ......... 435/69.1 |
| 2004/0221331 | A1* | 11/2004 | Albertsen et al. ............ 800/278 |
| 2005/0053959 | A1 | 3/2005 | Turck et al. |
| 2006/0123505 | A1* | 6/2006 | Kikuchi et al. ............... 800/278 |
| 2009/0119022 | A1 | 5/2009 | Timberlake et al. |

FOREIGN PATENT DOCUMENTS

| | | | |
|---|---|---|---|
| WO | WO 93/21334 A1 | 10/1993 | |
| WO | WO 97/06268 A2 | 2/1997 | |
| WO | WO 00/44223 A1 | 8/2000 | |
| WO | WO 00/44917 A1 | 8/2000 | |
| WO | WO01/09357 * | 2/2001 | ............ C12N 15/82 |
| WO | WO 01/09357 A2 | 2/2001 | |
| WO | WO 2005/098006 A1 | 10/2005 | |
| WO | WO 2006/005166 A1 | 1/2006 | |
| WO | WO 2006/124502 A2 | 11/2006 | |

OTHER PUBLICATIONS

Kulmburg et al. Specific binding sites for the activator protein, ALCR, in the alcA promoter of the ethanol regulon of Aspergillus nidulans. Journal of Biological Chemistry. 1992. 267(29): 21146-21153.*

Deveaux et al. The ethanol switch: a tool for tissue-specific gene induciton during plant development. The Plant Journal. 2003. 36: 918-930.*

Flipphi et al. Regulation of the Aldehyde Dehydrogenase Gene (aldA) and its role in the control of the coinducer level necessary for induction of the ethanol utilization pathway in Aspergillus nidulans. The Journal of Biological Chemistry. 2001. 276(10): 6950-6958.*

GenBank Accession No. AF260123. Aspergillus nidulans aldehyde dehydrogenase ALDH (aldA) gene. Published Nov. 28, 2008. pp. 1-3.*

Nikolaev et al. Unique DNA binding specificity of the binuclear zinc AlcR activator of the ethanol utilization pathway in Aspergillus nidulans. The Journal of Biological Chemistry. 1999. 274(14): 9795-9802.*

European Search Report Corresponding to Application No. PCT/US2011/065184; Dated Nov. 6, 2014; 7 pages.

Ait-ali et al. "Flexible control of plant architecture and yield via switchable expression of Arabidopsis gai", *Plant Biotechnology Journal*, 2003,1:337-343.

Benfey et al. "The Cauliflower Mosaic Virus 35S Promoter: Combinatorial Regulation of Transcription in Plants", *Science*, 250:959-966, 1990.

Bhattacharyya et al. "Analysis of cis-sequence of subgenomic transcript promoter from the Figwort Mosaic Virus and comparison of promoter activity with the cauliflower mosaic virus promoters in monocot and dicot cells", *Virus Research*, 2002, 90:47-62.

Caddick et al. "An ethanol inducible gene switch for plants used to manipulate carbon metabolism", *Nature Biotechnology*, vol. 16, Feb. 1998, 177-180.

Camargo et al. "Identification of genes responsive to the application of ethanol on sugarcane leaves", *Plant Cell Rep.*, 2007, 26:2119-2128.

Ellis et al. "Isolation of Alcohol Oxidase and Two Other Methanol Regulatable Genes from the Yeast Pichia pastoris", *Molecular and Cellular Biology*, vol. 5, No. 5, May 1985, 1111-1121.

Fang et al. "Multiple cis regulatory elements for maximal expression of the cauliflower mosaic virus 35S promoter in transgenic plants", *Plant Cell*, 1989;1:141-150.

Felenbok et al. "The ethanol regulon in Aspergillus nidulans: characterization and sequence of the positive regulatory gene alcR", *Gene*, 73, 1988, 385-396.

Flipphi et al. "Characteristics of physiological inducers of the ethanol utilization (alc) pathway in Aspergillus nidulans", *Biochem J.*, 2002, 364, 25-31.

Flipphi et al. "Functional analysis of alcs, a gene of the alc cluster in Aspergillus nidulans", *Fungal Genetics and Biology*, 43, 2006, 247-260.

Flipphi et al. "Regulation of the Aldehyde Dehydrogenase Gene (aldA) and Its Role in the Control of the Coinducer Level Necessary for Induction of the Ethanol Utilization Pathway in Aspergillus nidulans", *J. Biol. Chem.*, 2001, 276:6950-6958.

Fillinger et al. "The basal level of transcription of the alc genes in the ethanol regulon in Aspergillus nidulans is controlled both by the specific transactivator AlcR and the general carbon catabolite repressor CreA", *FEBS Letters*, 368, 1995, 547-550.

Garoosi et al. "Characterization of the ethanol-inducible alc gene expression system in tomato", *Journal of Experimental Botany*, vol. 56, No. 416, 1635-1642, Jun. 2005.

Gwynne et al. "Comparison of the cis-acting control regions of two coordinately controlled genes involved in ethanol utilization in Aspergillus nidulans", *Gene*, 51, 1987, 205-216.

Hedtke et al. "HEMA RNAi silencing reveals a control mechanism of ALA biosynthesis on Mg chelatase and Fe chelatase", *Plant Mol. Bio.* 64(6):733-742 (2007).

Hintz et al. "Improved gene expression in *Aspergillus nidulans*", *Canadian J. Bot.* 73:876-884 (1995).

Jia et al. "Combination of the ALCR/alcA ethanol switch and GAL4/VP16-UAS enhancer trap system enables spatial and temporal control of transgene expression in Arabidopsis", *Plant Biotechnol J.* 5(4):477-82 (2007).

Kulmburg et al. "Specific binding sites in the *alcR* and *alcA* promoters of the ethanol regulon for the CREA repressor mediating carbon catabolite repression in Aspergillus nidulans" *Mol. Microbiol.* 7(6): 847-857 (1993).

Kulmburg et al. "Identification of the promoter region involved in the autoregulation of the transcriptional activator ALCR in *Aspergillus nidulans*", *Mol. Cell. Biol.* 12(5):1932-1939 (1992).

Kulmburg et al. "Specific binding sites for the activator protein, ALCR, in the *alcA* promoter of the ethanol regulon of *Aspergillus nidulans*", *J Biol Chem.* 267(29):21146-53 (1992).

Laufs et al. "Separable roles of *UFO* during floral development revealed by conditional restoration of gene function", *Development*, 130:785-796 (2003).

Lenouvel et al. "In vitro recognition of the specific DNA targets by AlcR, a zinc binuclear cluster activator different from other proteins of this class", *J. Biol. Chem.* 272(24):15521-15526 (1997).

Li et al. "Ethanol inducible gene expression system and its applications in plant functional genomics", *Plant Science*, 169:463-469, 2005.

Lockington et al. "Cloning and characterization of the ethanol utilization regulon of *Aspergillus nidulans*", *Gene* 33:137-149 (1985).

Lockington et al. "Regulation of *alcR*, the positive regulatory gene of the ethanol utilization regulon of *Aspergillus nidulans*", *Mol. Microbiol.* 1(3): 275-281 (1987).

Loessl et al. "Inducible trans-activation of plastid transgenes: expression of the *R. eutropha* phb operon on transplastomic tobacco", *Plant Cell Physiol.* 46(9):1462-1471 (2005).

Maizel et al. "Temporally and spatially controlled induction of gene expression in Arabidopsis thaliana" *Plant J.* 38:164-171 (2004).

Mantis et al. "Characterization of the *Agrobacterium tumefaciens* heat shock response: evidence for a sigma-32 like sigma factor", *J. Bacteriol.* 174(3):991-997 (1992).

Mantis et al. "The *Agrobacterium tumefaciens* Vir gene transcriptional activator VirG is transcriptionally induced by acid pH and other stress stimuli", *J Bacteriol.* 174(4):1189-1196 (1992).

Mathieu et al. "In vivo studies of the upstream regulatory *cis*-acting elements of the *alcR* gene encoding the transactivator of the ethanol regulon in *Aspergillus nidulans*" *Mol. Microbiol.* 36(1):123-131 (2000).

Mathieu et al. "Patterns of nucleosomal organization in the *alc* regulon of *Aspergillus nidulans*: roles of the AlcR transcriptional activator and the CreA global repressor" Mol. Microbiol. 56(2):535-548 (2005).

(56) References Cited

OTHER PUBLICATIONS

Mathieu et al., "The *Aspergillus nidulans* CREA protein mediates glucose repression of the ethanol regulon at various levels through competition the ALCR-specific transactivator" *EMBO J.* 13(17): 4022-4027 (1994).

Mitsuhara et al. "Efficient promoter cassettes for enhanced expression of foreign genes in dicotyledonous and monocotyledonous plants", *Plant Cell Physiol.* 37(1):49-59 (1996).

Nikolaev et al. "Heterologous expression of the *Aspergillus nidulans* alcR-alcA system in *Aspergillus niger*", *Fungal Genetics & Biology*, 37(1):89-97 (2002).

Nikolaev et al. "Unique DNA binding specificity of the binuclear zinc AlcR activator of the ethanol utilization pathway of *Aspergillus nidulans*", *J. Biol. Chem.* 274(14):9795-9802 (1999).

Odell et al. "Identification of DNA sequences required for activity of the cauliflower mosaic virus 35S promoter", *Nature* 313:810-812 (1985).

Ow et al. "Functional regions of the cauliflower mosaic virus 35S RNA promoter determined by the use of the firefly luciferase gene as a reporter of promoter activity", *Proc. Natl. Acad. Sci. USA* 84:4870-4874 (1987).

Panozzo et al. "The zinc binuclear cluster activator AlcR is able to bind to single sites but requires multiple repeated sites for synergistic activation of the *alcA* gen in *Aspergillus nidulans*", *J. Biol. Chem.* 272(36):22859-22865 (1997).

Panozzo et al. "The CreA repressor is the sole DNA-binding protein responsible for carbon catabolite repression of the *alcA* gene in *Aspergillus nidulans* via its binding to a couple of specific sites", *J. Biol. Chem*, 273(11): 6367-6372.

Pasquali et al. "Versatile transformation vectors to assay the promoter activity of DNA elements in plants", *Gene* 149:373-374 (1994).

Peebles et al. "Characterization of an ethanol-inducible promoter system in *Catharanthus roseus* hairy roots" *Biotechnol. Progress* 23(5):1258-1260 (2007).

Roberts et al. "Tailoring chemically induced gene switches for research and agriculture" ISB News Report (Nov. 2005), 3 pages.

Roberts et al. "The alc-GR system: a modified alc gene switch designed for use in plant tissue culture", *Plant Physiol* 138(3):1259-67 (2005).

Sakvarelidze et al. Coupling the GAL4 UAS system with alcR for versatile cell type-specific chemically inducible gene expression in Arabidopsis. *Plant Biotechnol. J.* 5(4):465-76 (2007).

Salter et al. "Characterisation of the ethanol-inducible *alc* gene expression system for transgenic plants" *Plant J.* 16(1):127-132 (1998).

Schaarschmidt et al. "Local induction of the alc gene switch in transgenic tobacco plants by acetaldehyde", *Plant Cell Physiol.* 45(11):1566-77 (2004).

Topp et al. "Alcohol induced silencing of gibberellin 20-oxidases in *Kalanchoe blossfeldiana*", *Plant Cell, Tissue Organ Culture* 93:241-248 (2008).

Waring et al. "Characterization of an inducible expression system in *Aspergillus nidulans* using alcA and tubulin-coding genes" *Gene* 79:119-130 (1989).

Notification Concerning Transmittal of International Preliminary Report on Patentability in corresponding PCT Application No. PCT/US2011/065184 mailed Aug. 1, 2013 (7 pages).

Deveaux et al. "The ethanol switch: a tool for tissue-specific gene induction during plant development," *The Plant Journal*, Blackwell Scientific Publications, 36: 918-930 (Jan. 1, 2003).

European Search Report Corresponding to Application No. PCT/US2011065184; Dated:Nov. 21, 2014; 5 pages.

Hintz et al. "A glucose-derepressed promoter for expression of heterologous products in the filamentous fungus *Aspergillus nidulans,*" *Bio/Technology* (Nature Publishing Company). 11(7):815-818 (Jul. 1993).

\* cited by examiner

METHODS AND COMPOSITIONS FOR MODIFIED ETHANOL INDUCIBLE PROMOTER SYSTEMS

STATEMENT OF PRIORITY

This application is a 35 U.S.C. §371 national phase application of International Application Serial No. PCT/US2011/065184, filed Dec. 15, 2011, which claims the benefit, under 35 U.S.C. §119 (e), of U.S. Provisional Application No. 61/433,658; filed Jan. 18, 2011, the entire contents of which are incorporated by reference herein.

FIELD OF THE INVENTION

The present invention is directed generally to the field of expression of nucleic acids. Specifically, this invention relates to methods of making promoters inducible and expression systems and plants, plant parts and plant cells comprising the inducible promoters.

BACKGROUND

Improvement in crop productivity, quality and/or resistance to pests, for example, requires the manipulation and expression of both heterologous and endogenous genes in plants and plant tissues. Methods of controlling gene expression include the use of appropriate promoters and other regulators of expression. Through the use of carefully selected promoters, it is possible to control the expression of a particular gene or nucleotide sequence. Promoters can be constitutive (i.e., activated all of the time), developmentally regulated (i.e., activated in response to a particular developmental stage, for example, embryogenesis, senescence, and the like), tissue-specific (i.e., activated only in certain plant tissues, for example, in the root, leaf, seed, and the like), environmentally regulated (for example, activated by temperature and/or light) and/or chemically inducible (i.e., activated by the presence of a particular chemical compound or group of compounds that includes both endogenous and exogenous compounds).

Promoters which are inducible by the external application of a chemical inducer allow control of expression of a nucleotide sequence or gene that is operably associated with the inducible promoter at various stages of plant growth and development as desired. Thus, for example, using a chemically inducible promoter, a plant can be produced that conditionally expresses herbicide or pesticide resistance or that is induced to synchronously produce flowers.

The present invention addresses previous shortcomings in the art by providing compositions and methods for producing promoters that have a pattern of inducibility that is similar to that of the alcohol dehydrogenase (ADH1) system of *Aspergillus nidulans* using promoters that are not naturally inducible by compounds that induce ADH1 system of *A. nidulans*.

SUMMARY OF THE INVENTION

In one aspect, the present invention provides an isolated nucleic acid molecule comprising, consisting essentially of, or consisting of one or more nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order.

In additional aspects, the present invention provides an isolated nucleic acid molecule comprising, consisting essentially of, or consisting of one or more nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order, wherein the one or more nucleotide sequences are operably linked to a promoter, further wherein the promoter is operably linked to a nucleotide sequence of interest.

It is further contemplated that a nucleic acid molecule, a nucleic acid construct, and/or a composition of this invention can be employed in various methods. Thus, the present invention additionally provides a method of making a promoter inducible, comprising: a) constructing a nucleic acid molecule comprising, consisting essentially of, or consisting of at least two nucleotide sequences, each encoding an inverted repeat, said at least two nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order; and b) operably linking the nucleic acid molecule of (a) with the promoter. In a further aspect, a method is provided of making a promoter inducible comprising: a) constructing a nucleic acid molecule comprising, consisting essentially of, or consisting of two to nine (e.g., 2, 3, 4, 5, 6, 7, 8 or 9) nucleotide sequences each encoding an inverted repeat, said two to nine nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order; and b) operably linking the nucleic acid molecule of (a) with the promoter.

The present invention additionally provides a method of making a promoter inducible, comprising: a) constructing a nucleic acid molecule comprising, consisting essentially of, or consisting of at least five nucleotide sequences, each encoding an inverted repeat, said at least five nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order; and b) operably linking the nucleic acid molecule of (a) with the promoter. In a further aspect, a method of making a promoter inducible is included, which comprises: a) constructing a nucleic acid molecule comprising, consisting essentially of, or consisting of five to nine (e.g., 5, 6, 7, 8 or 9) nucleotide sequences each encoding an inverted repeat, said five to nine nucleotide sequences selected from the group consisting of the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, in any combination, in any orientation, and/or in any order; and b) operably linking the nucleic acid molecule of (a) with the promoter. The present invention additionally provides a method of making the expression of a nucleotide sequence of interest inducible, comprising: operably linking a promoter of this invention (e.g., a promoter that has been made inducible according to the methods described herein) with the nucleotide sequence of interest, thereby making the expression of the nucleotide sequence of interest inducible.

Additional aspects of the invention include compositions comprising nucleic acid constructs comprising a promoter of the present invention as well as plants, plant parts and/or plant cells comprising the compositions, nucleic acid constructs, nucleic acid molecules, nucleotide sequences and/or promoters of the invention.

These and other aspects of the invention are set forth in more detail in the description of the invention below.

DETAILED DESCRIPTION OF THE INVENTION

Figure 1:
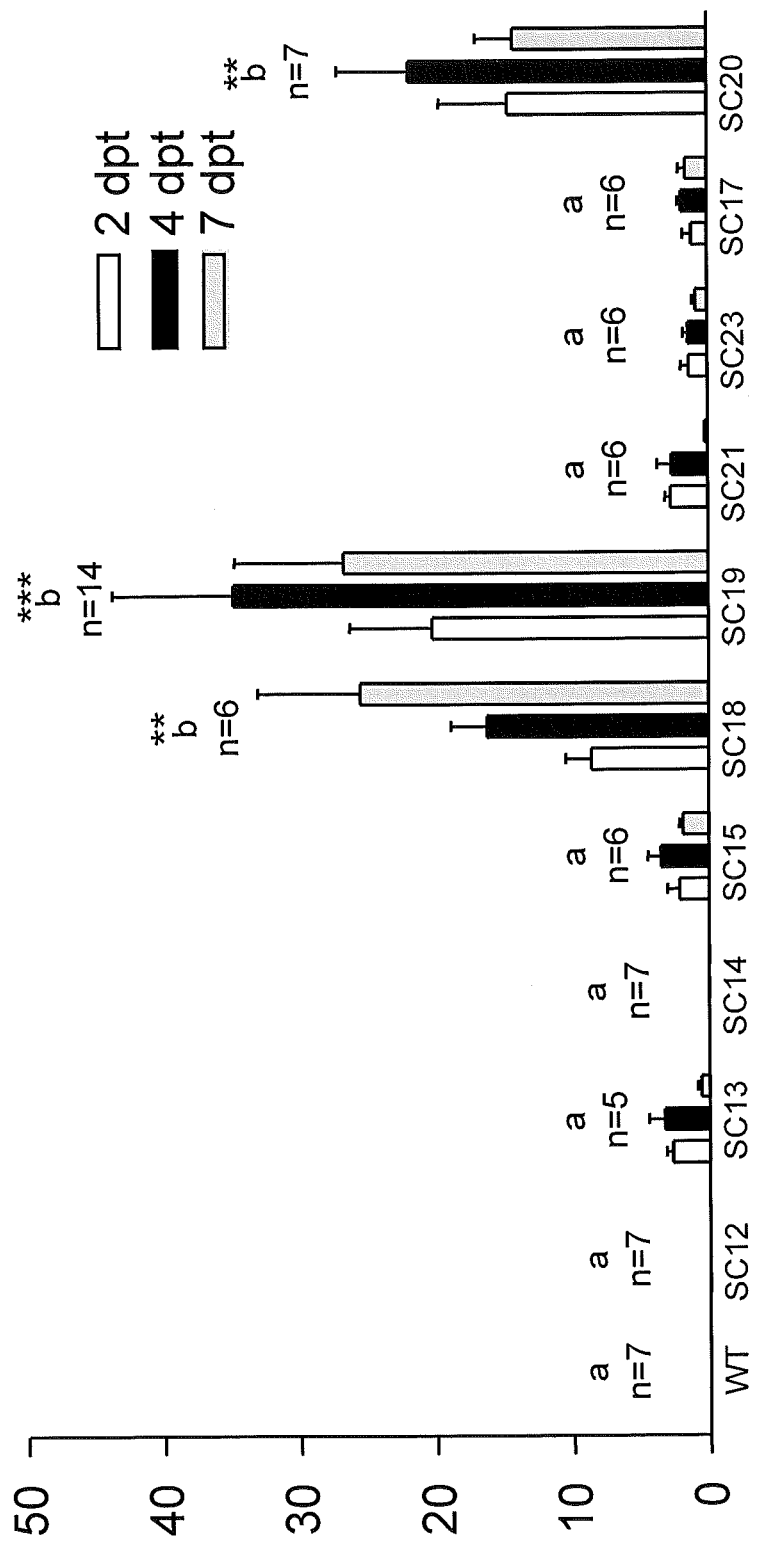
FIG. 1 shows the results for ethanol inducible GUS expression at two days, four days and seven days post treatment of six month old transgenic sugar cane plants containing the different ethanol switch constructs. n=number of independent, single copy transgenic plants analyzed for each construct. Data with different letters are significantly different (P<0.01; *P<0.001).

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

In some embodiments, the present invention provides an isolated nucleic acid molecule comprising one or more nucleotide sequences selected from the group consisting of a nucleotide sequence of SEQ ID NO:1, SEQ ID NO:3, SEQ ID NO:4, SEQ ID NO:5, SEQ ID NO:6, SEQ ID NO:7, SEQ ID NO:8, and SEQ ID NO:10 in any combination, in any orientation, and/or in any order, including but not limited to multiples of the same nucleotide sequence.

The nucleotide sequences of the present invention, e.g., the nucleotide sequence of SEQ ID NO:1, SEQ ID NO:3, SEQ ID NO:4, SEQ ID NO:5; SEQ ID NO:6; SEQ ID NO:7, SEQ ID NO:8, and SEQ ID NO:10, comprise, consist essentially of, or consist of inverted repeats of the alcR inverted repeat binding sites, or variants thereof, of the *A. nidulans* alcohol dehydrogenase system (ADH1). Thus, SEQ ID NO:1 provides the nucleotide sequence of $n_y$ GCGGNNCCGC$n_y$. N or n can be independently any nucleic acid base (A, G, C, or T) and y can be independently any number, as set forth below. Additional nucleotide sequences of the invention are as follows: ATGCA TGCGGAACCGCACGAGG (SEQ ID NO:3); GGCCAT GCGGAGCCGCACGCGT (SEQ ID NO:4); ACAAG AGCGGCTCCGCTTGACC (SEQ ID NO:5); TACGT AGCGGAACCGCTGCTCC (SEQ ID NO:6); TACCA TGCGGAACCGCACGTCC (SEQ ID NO:7); ATGCA TGCGGTGCCGCACGAGG (SEQ ID NO:8); and TACGT TGCGGAACCGCAGCTCC (SEQ ID NO:10).

In some embodiments, the nucleotide sequences of the invention can comprise one or more nucleotides (i.e., bases) between the inverted repeats (e.g., an intervening sequence). Thus, in certain embodiments, the number of nucleotides comprising the intervening sequence can be two (i.e., N=2) (e.g., SEQ ID NO:1=$n_y$GCGG<u>NN</u>CCGC$n_y$, (intervening sequence bolded and underlined)). Non-limiting examples of the intervening sequence include TT, AA, GG, CC, TA, TG, TC, AT, AG, AC, GT, GC, GA, CA, CT, or CG, and the like. Thus, any 2-mer can be used as an intervening sequence in SEQ ID NO:1, respectively.

In some embodiments, SEQ ID NO:1 (<u>$n_y$</u>GCG-GNNCCGC<u>$n_y$</u>, (flanking sequences bolded and underlined)) of the present invention can comprise zero to 100 or more nucleotides (i.e., bases) that flank the right and/or left side of the inverted repeats (e.g., a flanking sequence, $n_y$). The flanking sequences (i.e., $n_y$) can be of any length and/or composition of nucleotides, wherein each nucleotide can be independently adenine, thymine, guanine and/or cytosine (i.e., wherein n=A, T, G, and/or C), in any combination and/or in any order. Thus, in some embodiments of the invention, y is independently zero to 100 nucleotides. Thus, the number of nucleotides in a flanking sequence can be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, wherein each nucleotide in a flanking sequence can be independently adenine, thymine, guanine and/or cytosine, in any combination and/or in any order. As one of ordinary skill in the art would appreciate, flanking sequences of any length and composition can be produced that are included within SEQ ID NO:1 of the present invention according to art-known methods.

In some embodiments, the isolated nucleic acid molecule of the present invention can comprise, consist essentially of, or consist of one or more nucleotide sequences of the present invention (i.e., SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10). Thus, in some embodiments, the nucleic acid molecule can comprise, consist essentially of, or consist of, for example, one, two, three, four, five, six, seven, eight, nine, ten, eleven, twelve, thirteen, fourteen, fifteen, sixteen, etc., nucleotide sequences of SEQ ID NO:1, SEQ ID NO:3, SEQ ID NO:4, SEQ ID NO:5; SEQ ID NO:6; SEQ ID NO:7, SEQ ID NO:8, and/or SEQ ID NO:10, in any combination, in any orientation, and/or in any order. Thus, in some embodiments, the nucleic acid molecules of the present invention can comprise a multimer of the nucleotide sequences of SEQ ID NO:1, SEQ ID NO:3, SEQ ID NO:4, SEQ ID NO:5; SEQ ID NO:6; SEQ ID NO:7, SEQ ID NO:8, and/or SEQ ID NO:10, wherein the nucleotide sequences of the multimer (e.g., the nucleic acid molecule) can be the same and/or different from one another, in any combination, in any orientation, and/or in any order. In further embodiments, the isolated nucleic acid molecule comprising only one nucleotide sequence of SEQ ID NO:1, SEQ ID NO:3, SEQ ID NO:4, SEQ ID NO:5; SEQ ID NO:6; SEQ ID NO:7, SEQ ID NO:8, and/or SEQ ID NO:10, does not comprise only one nucleotide sequence of SEQ ID NO:3, SEQ ID NO:4, or SEQ ID NO:5.

Thus, in some aspects of the present invention, the number of nucleotide sequences in an isolated nucleic acid molecule of this invention can be in a range from one nucleotide sequence to about nine nucleotide sequences, from one nucleotide sequence to about ten nucleotide sequences, from one nucleotide sequence to about eleven nucleotide sequences, from one nucleotide sequence to about twelve nucleotide sequences, from one nucleotide sequence to about thirteen nucleotide sequences, from one nucleotide sequence to about fourteen nucleotide sequences, from one nucleotide sequence to about fifteen nucleotide sequences, from about two nucleotide sequences to about five nucleotide sequences, from about two nucleotide sequences to about seven nucleotide sequences, from about two nucleotide sequences to about nine nucleotide sequences, from about two nucleotide sequences to about ten nucleotide sequences, from about two nucleotide sequences to about eleven nucleotide sequences, from about two nucleotide sequences to about twelve nucleotide sequences, from about two nucleotide sequences to about thirteen nucleotide sequences, from about two nucleotide sequences to about fourteen nucleotide sequences, from about two nucleotide sequences to about fifteen nucleotide sequences, from about three nucleotide sequences to about five nucleotide sequences, from about three nucleotide sequences to about seven nucleotide sequences, from about three nucleotide sequences to about nine nucleotide sequences, from about three nucleotide sequences to about ten nucleotide sequences, from about three nucleotide sequences to about eleven nucleotide sequences, from about three nucleotide sequences to about twelve nucleotide sequences, from about three nucleotide sequences to about thirteen nucleotide sequences, from about three nucleotide sequences to about fourteen nucleotide sequences, from about three nucleotide sequences to about fifteen nucleotide sequences, from about four nucleotide sequences to about nine nucleotide sequences, from about four nucleotide sequences to about ten nucleotide sequences, from about four nucleotide sequences to about eleven nucleotide sequences, from about four nucleotide sequences to about twelve nucleotide sequences, from about four nucleotide sequences to about thirteen nucleotide sequences, from about four nucleotide sequences to about fourteen nucleotide sequences, from about four nucleotide sequences to about fifteen nucleotide sequences, from about five nucleotide sequences to about nine nucleotide sequences, from about five nucleotide sequences to about ten nucleotide sequences, from about five nucleotide sequences to about eleven nucleotide sequences, from about five nucleotide sequences to about twelve nucleotide sequences, from about five nucleotide sequences to about thirteen nucleotide sequences, from about five nucleotide sequences to about fourteen nucleotide sequences, from about five nucleotide sequences to about fifteen nucleotide sequences, from about six nucleotide sequences to about nine nucleotide sequences, from about six nucleotide sequences to about ten nucleotide sequences, from about six nucleotide sequences to about eleven nucleotide sequences, from about six nucleotide sequences to about twelve nucleotide sequences, from about six nucleotide sequences to about thirteen nucleotide sequences, from about six nucleotide sequences to about fourteen nucleotide sequences, from about six nucleotide sequences to about fifteen nucleotide sequences, from about seven nucleotide sequences to about nine nucleotide sequences, from about seven nucleotide sequences to about ten nucleotide sequences, from about seven nucleotide sequences to about eleven nucleotide sequences, from about seven nucleotide sequences to about twelve nucleotide sequences, from about seven nucleotide sequences to about thirteen nucleotide sequences, from about seven nucleotide sequences to about fourteen nucleotide sequences, from about seven nucleotide sequences to about fifteen nucleotide sequences, from about eight nucleotide sequences to about ten nucleotide sequences, from about eight nucleotide sequences to about eleven nucleotide sequences, from about eight nucleotide sequences to about twelve nucleotide sequences, from about eight nucleotide sequences to about thirteen nucleotide sequences, from about eight nucleotide sequences to about fourteen nucleotide sequences, from about eight nucleotide sequences to about fifteen nucleotide sequences, from about nine nucleotide sequences to about eleven nucleotide sequences, from about nine nucleotide sequences to about twelve nucleotide sequences, from about nine nucleotide sequences to about thirteen nucleotide sequences, from about nine nucleotide sequences to about fourteen nucleotide sequences, from about nine nucleotide sequences to about fifteen nucleotide sequences, and the like.

In some embodiments of the present invention, the isolated nucleic acid molecule of this invention comprises, consists essentially of, or consists of at least two nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In other embodiments of the present invention, the isolated nucleic acid molecule of this invention comprises, consists essentially of, or consists of at least three nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In still other embodiments, the isolated nucleic acid molecule of this invention comprises, consists essentially of or consists of at least five nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In additional embodiments, the isolated nucleic acid molecule of this invention comprises, consists essentially of, or consists of about two to about nine nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In further embodiments, the isolated nucleic acid molecule of the invention comprises, consists essentially of, or consists of about three to about nine nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In still further embodiments, the isolated nucleic acid molecule of the invention comprises, consists essentially of, or consists of about five to about nine nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order. In other embodiments, the isolated nucleic acid molecule of the invention comprises, consists essentially of, or consists of about five to about fifteen nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order.

As discussed above, the isolated nucleic acid molecule comprising multimers of the nucleotide sequences of the present invention can comprise, consist essentially of, or consist of multimers of any of the nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any number of copies of a particular nucleotide sequence of the invention and/or in any combination, in any orientation, and/or in any order of the nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10. Thus, in some embodiments the isolated nucleic acid molecule can comprise, consist essentially of, or consist of multiple copies of the same nucleotide sequence (e.g., 2 copies, 3 copies, 4 copies, 5 copies, 6 copies, 7 copies, 8 copies, 9 copies, 10 copies, 11 copies, 12 copies, etc.). In other embodiments, the isolated nucleic acid molecule can comprise, consist essentially of, or consist of multiple nucleotide sequences of the present invention each of which are different from one another. In additional embodiments, the present invention provides nucleic acid molecules comprising, consisting essentially of, or consisting of multimers of the nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, wherein some of the nucleotide sequences are the same (i.e., particular sequences are present in multiple copies) and some of the nucleotide sequences are different from one another, in any combination, in any orientation, and/or in any order.

Thus, a non-limiting example of a multimer of the nucleotide sequences of the present invention includes (SEQ ID NO:1)$_x$ (SEQ ID NO:3)$_x$(SEQ ID NO:4)$_x$(SEQ ID NO:5)$_x$ (SEQ ID NO:6)$_x$(SEQ ID NO:7)$_x$(SEQ ID NO:8)$_x$ (SEQ ID NO:10)$_x$, wherein x is independently 0 to 9 or more (e.g., 0, 1, 2, 3, 4, 5, 6, 7, 8, 9, etc.). Further non-limiting examples of multimers of the nucleotide sequences of the present invention include (SEQ ID NO:1)$_4$; (SEQ ID NO:5)(SEQ ID NO:3)(SEQ ID NO:10); (SEQ ID NO:1)(SEQ ID NO:5) (SEQ ID NO:3)(SEQ ID NO:4); (SEQ ID NO:1)$_2$(SEQ ID NO:6)$_4$(SEQ ID NO:3)$_3$; (SEQ ID NO:1)$_2$(SEQ ID NO:6) (SEQ ID NO:3)(SEQ ID NO:4)$_2$; (SEQ ID NO:5)$_3$(SEQ ID NO:3)(SEQ ID NO:4); (SEQ ID NO:1)(SEQ ID NO:5)$_2$ (SEQ ID NO:3)$_2$; (SEQ ID NO:6)$_4$ (SEQ ID NO:4)$_2$; (SEQ ID NO:1)(SEQ ID NO:6)$_2$; (SEQ ID NO:1)(SEQ ID NO:5) (SEQ ID NO:3)(SEQ ID NO:4)$_2$; (SEQ ID NO:1)$_2$(SEQ ID NO:6)$_2$(SEQ ID NO:3)$_2$; (SEQ ID NO:1)$_2$(SEQ ID NO:3)$_3$(SEQ ID NO:10)); (SEQ ID NO:3)(SEQ ID NO:4)$_3$; (SEQ ID NO:1)(SEQ ID NO:5)$_5$(SEQ ID NO:4); (SEQ ID NO:1)(SEQ ID NO:4)(SEQ ID NO:5)(SEQ ID NO:8)(SEQ ID NO:10); (SEQ ID NO:5)$_3$(SEQ ID NO:8); (SEQ ID NO:5)$_2$(SEQ ID NO:6)(SEQ ID NO:7)(SEQ ID NO:8)$_2$; (SEQ ID NO:6)$_4$; (SEQ ID NO:5)(SEQ ID NO:4)(SEQ ID NO:6)(SEQ ID NO:10)(SEQ ID NO:8)(SEQ ID NO:1); (SEQ ID NO:8)$_4$(SEQ ID NO:10)$_2$; (SEQ ID NO:3)(SEQ ID NO:5)$_2$; (SEQ ID NO:6)(SEQ ID NO:10); (SEQ ID NO:3) (SEQ ID NO:4)$_2$(SEQ ID NO:7)$_2$; (SEQ ID NO:10)$_6$; (SEQ ID NO:3)$_3$; (SEQ ID NO:5)$_3$(SEQ ID NO:10)$_4$; (SEQ ID NO:3)(SEQ ID NO:7)$_3$; (SEQ ID NO:1)(SEQ ID NO:4)$_5$ (SEQ ID NO:10)$_4$, (SEQ ID NO:3)$_8$, and the like.

In some embodiments, the nucleic acid molecules comprising multimers of the nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, can further comprise one or more nucleotides (i.e., bases) between each of the inverted repeats (i.e., the nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10) (e.g., a spacer sequence). The spacer sequences can be of any length and composition of nucleotides, wherein each nucleotide can be independently adenine, thymine, guanine and/or cytosine (i.e., wherein n=A, T, G, or C), in any order and/or in any combination, and y is independently 0-100 nucleotides or more. In some embodiments of the present invention, the spacer sequences are the same as (i.e., equivalent to) the flanking sequences (i.e, $n_y$) described herein. Thus, in some embodiments, the nucleic acid molecule of the present invention comprises, consists essentially of, or consists of spacer sequences (i.e., flanking sequences, $n_y$) that can be the same as one another (i.e., the same as other spacer sequences of the nucleic acid molecule) and/or different than one another, or any combination thereof. A non-limiting example of a multimer of the present invention comprising a spacer sequence is the following: nnnnnGCGGNNCCGCnnnnn<u>nnnnnnnnnnn</u>GCG-GNNCCGCnnnnn<u>nnnnnnnnnn</u>GCGGNNC CGCnnnnn; (SEQ ID NO:1)$_3$, wherein y=5. In this example, the spacer sequences are bolded and underlined and are shown to be of different lengths. Further non-limiting examples of a multimer of the present invention comprising a spacer sequence is the following: (1) nnnnnGCGGNNCCGC <u>nnnnnnnnnn</u>GCGGNNCCGC <u>nnnnnnnnnn</u>GCGGNN-CCGCnnnnn; (SEQ ID NO:1)$_3$, wherein y=5; and (2) nnnnnGCGGNNCCGCnnnnnnnnnnnnn GCGGNNC-CGCnnnnnnnnnGCGGNNCCGCnnnnn; (SEQ ID NO:1)$_3$, wherein y=5 or 7. In these two examples, the bolded and underlined nucleotides represent both the spacer sequences and the flanking sequences of the nucleotide sequences that comprise the multimer (i.e., in these examples, the spacer sequences are equivalent to the flanking sequences).

In another aspect, the present invention further includes an isolated nucleic acid molecule comprising, consisting of, or consisting essentially of one or more nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order, wherein the one or more nucleotide sequences are operably linked to a promoter, thereby making the promoter inducible by contact with a chemical compound that can induce the expression of the alcohol dehydrogenase system of *A. nidulans*. The promoter can be any promoter. In some embodiments, the promoter can be a promoter that is naturally inducible by chemical compounds that can induce the expression of the alcohol dehydrogenase system of *A. nidulans*, thereby making a promoter that has an increased level of inducibility, and/or an increased sensitivity to the inducing compounds, as compared to the native promoter.

In additional aspects, the present invention provides an isolated nucleic acid molecule comprising, consisting of, or consisting essentially of one or more nucleotide sequences of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order, wherein the one or more nucleotide sequences are operably linked to a promoter, further wherein the promoter is operably linked to a nucleotide sequence of interest, thereby making the expression of the nucleotide sequence of interest inducible by contact with a chemical compound that can induce the expression of the alcohol dehydrogenase system of *A. nidulans*. In some embodiments, when the one or more nucleotide sequences (e.g., SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order) are operably linked to a promoter that is naturally inducible by contact with a chemical compound that can induce the expression of the alcohol dehydrogenase system of *A. nidulans*, the expression of the nucleotide sequence of interest that is then operably linked to said promoter is increased, made more sensitive and or made more specific in response to the chemical inducer as compared to the expression of the nucleotide sequence of interest when it is operably linked to the native promoter. Thus, the present invention provides a method of making the expression of a nucleotide sequence of interest inducible (or have increased inducibility, and/or increased sensitivity) comprising operably linking a promoter of the present invention (e.g., a promoter that is operably linked to one or more nucleotide sequences of any of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any combination, in any orientation, and/or in any order) to the nucleotide sequence of interest, thereby making the expression of the nucleotide sequence of interest inducible (or have increased inducibility and/or increased sensitivity).

Accordingly, the present invention provides a method of making a promoter inducible, or making a promoter that has increased inducibility and/or increased sensitivity in response to a chemical compound that can induce the expression of the alcohol dehydrogenase system of *A. nidulans* as compared to the native promoter, comprising: a) constructing a nucleic acid molecule comprising one or more nucleotide sequences each encoding an inverted repeat, said one or more nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and SEQ ID NO:10, in any combination, in any orientation, and/in any order; and b) operably linking the nucleic acid molecule of (a) with the promoter. In some embodiments of the present invention, wherein when the nucleotide sequence selected is only SEQ ID NO:3, or only SEQ ID NO:4, or only SEQ ID NO:5, at least two copies of SEQ ID NO:3, SEQ ID NO:4, or SEQ ID NO:5 are present (e.g., (SEQ ID NO:3)$_2$, (SEQ ID NO:3)$_3$, (SEQ ID NO:4)$_2$, (SEQ ID NO:4)$_3$, (SEQ ID NO:5)$_2$, or (SEQ ID NO:5)$_3$, and the like).

In other embodiments of the present invention, a method of making a promoter inducible (or making a promoter that has increased inducibility and/or increased sensitivity) (by a chemical compound that can induce the expression of the alcohol dehydrogenase system of *A. nidulans*) is provided, comprising: a) constructing a nucleic acid molecule comprising at least two nucleotide sequences each encoding an inverted repeat, said at least two nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and SEQ ID NO:10, in any order, in any orientation, and/or in any combination; and b) operably linking the nucleic acid molecule of (a) with the promoter.

In additional embodiments of the present invention, a method of making a promoter inducible (by a chemical compound that can induce the expression of the alcohol dehydrogenase system of *A. nidulans*) (or making a promoter that has increased inducibility and/or increased sensitivity to said chemical compound) is provided, comprising: a) constructing a nucleic acid molecule comprising at least three nucleotide sequences each encoding an inverted repeat, said at least three nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and SEQ ID NO:10, in any order, in any orientation, and/or in any combination; and b) operably linking the nucleic acid molecule of (a) with the promoter.

In further embodiments of the present invention, a method of making a promoter inducible (e.g., inducible by a chemical compound that can induce the expression of a gene of the alcohol dehydrogenase system of *A. nidulans*) (or making a promoter that has increased inducibility and/or increased sensitivity to said chemical compound) is provided comprising: a) constructing a nucleic acid molecule comprising at least five nucleotide sequences each encoding an inverted repeat, said at least five nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination; and b) operably linking the nucleic acid molecule of (a) with the promoter.

In some embodiments, the present invention provides a method of making a promoter inducible (e.g., inducible by a chemical compound that can induce the expression of a gene of the alcohol dehydrogenase system of *A. nidulans*) (or making a promoter that has increased inducibility and/or increased sensitivity to said chemical compound), comprising: a) constructing a nucleic acid molecule comprising two to nine nucleotide sequences each encoding an inverted repeat, said two to nine nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination; and b) operably linking the nucleic acid molecule of (a) with the promoter.

In other embodiments, the present invention provides a method of making a promoter inducible (e.g., inducible by a chemical compound that can induce the expression of a gene of the alcohol dehydrogenase system of *A. nidulans*) (or making a promoter that has increased inducibility and/or increased sensitivity to said chemical compound), comprising: a) constructing a nucleic acid molecule comprising three to nine nucleotide sequences each encoding an inverted repeat, said three to nine nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination; and b) operably linking the nucleic acid molecule of (a) with the promoter.

In additional embodiments, the present invention provides a method of making a promoter inducible (e.g., inducible by a chemical compound that can induce the expression of a gene of the alcohol dehydrogenase system of *A. nidulans*) (or making a promoter that has increased inducibility and/or increased sensitivity to said chemical compound), comprising: a) constructing a nucleic acid molecule comprising five to nine nucleotide sequences each encoding an inverted repeat, said five to nine nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination; and b) operably linking the nucleic acid molecule of (a) with the promoter.

In some embodiments of the present invention, the nucleotide sequences encoding the inverted repeats can be present at or near the 5' end of the nucleic acid molecule. Thus, for example, the present invention provides a method of making a promoter comprising: a) constructing a nucleic acid molecule comprising at the 5' end at least five nucleotide sequences each encoding an inverted repeat, said at least five nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination; and b) operably linking the nucleic acid molecule of (a) with the promoter.

The present invention further comprises a method of making the expression of a nucleotide sequence of interest inducible, comprising operably linking an inducible promoter of the present invention to the nucleotide sequence of interest, thereby making the expression of the nucleotide sequence of interest inducible upon contact with a chemical compound that can induce the expression of the alcohol dehydrogenase system of *A. nidulans*. In some embodiments, when the promoter is a promoter that is naturally inducible by contact with a chemical compound that can induce the expression of the alcohol dehydrogenase system of *A. nidulans*, the expression of the nucleotide sequence of interest that is operably linked to said promoter is increased (increased induction), made more sensitive and or made more specific to the chemical compounds as compared to the expression of the nucleotide sequence of interest when it is operably linked to the native or wild-type inducible promoter.

In further embodiments, the nucleic acid molecules of the present invention can comprise a nucleotide sequence of interest operably linked to a promoter of the present invention, wherein the promoter is not operably linked to only one nucleotide sequence of SEQ ID NO:3, SEQ ID NO:4 or SEQ ID NO:5.

As used herein, the term "promoter" refers to a region of a nucleotide sequence that incorporates the necessary signals for the efficient expression of a coding sequence operably associated with the promoter. This may include sequences to which an RNA polymerase binds, but is not limited to such sequences and can include regions to which other regulatory proteins bind, together with regions involved in the control of protein translation and can also include coding sequences. Furthermore, a "promoter" of this invention is a promoter (e.g., a nucleotide sequence) capable of initiating transcription of a nucleic acid molecule in a cell of a plant.

Any promoter can be made inducible by the methods of the present invention. Promoters useable with the present invention can include those that drive expression of a nucleotide sequence constitutively, those that drive expression when induced, and those that drive expression in a tissue- or developmentally-specific manner, as these various types of promoters are known in the art and can be made inducible by the methods of the present invention.

In some embodiments of the present invention, a "minimal promoter" is used. A minimal promoter is a promoter having only the nucleotides/nucleotide sequences from a selected promoter that are required for binding of the transcription factors and transcription of a nucleotide sequence of interest that is operably associated with the minimal promoter including but not limited to TATA box sequences. These portions or sequences from a promoter are generally placed upstream (i.e., 5') of a nucleotide sequence to be expressed. Thus, nucleotides/nucleotide sequences from any promoter useable with the present invention can be selected for use as a minimal promoter. Any promoter may be altered to generate a minimal promoter by progressively removing nucleotides from the promoter until the promoter ceases to function in order to identify the minimal promoter. Thus, the smallest fragment of a promoter which still functions as a promoter is also considered a minimal promoter.

Accordingly, the present invention provides a method of making a promoter or minimal promoter that is inducible by any compound that can induce the expression of the alcohol dehydrogenase system of *A. nidulans*. Non-limiting examples of chemical compounds that can induce the promoters of the present invention (e.g., inducer compound) include a primary alcohol, a primary monoamine, a ketone, a $C_3$ to $C_9$ ketone. a methyl ketone, a hydrolysable ester, an aliphatic aldehyde, ethanol, allyl alcohol acetaldehyde, ethyl methyl ketone, acetone, ethylamine, cyclohexanone, butan-2-ol, 3-oxobutyric acid, propan-2-ol, propan-1-ol, butan-2-ol, threonine, and/or any combination thereof.

An inducer compound can be provided in any concentration that is not toxic to the plant. Thus, in some embodiments, the concentration of the inducer compound is about 0.01% to about 10% (v/v) or more. In other embodiments of the present invention, the concentration of the inducer compound is about 0.1% to about 20% (v/v). In still other embodiments of the invention, the concentration of the inducer compound is about 0.1% to about 5% (v/v). In further embodiments of the present invention, the concentration of the inducer compound is about 1% to about 2%. Thus, for example, the concentration of the inducer compound can be about 0.01%, about 0.02%, about 0.03%, about 0.04%, about 0.05%, about 0.06%, about 0.07%, about 0.08%. about 0.09%, about 0.1%, about 0.15%, about 0.2%, about 0.25%, about 0.3%, about 0.35%, about 0.4%, about 0.45%, about 0.6%. about 0.65%, about 0.7%, about 0.75%, about 0.8%, about 0.85%, about 0.9%, about 0.95%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% (v/v), and the like, and any combination thereof.

The inducer compound can be provided as a root drench, a spray, a mist, a suspension, an emulsion, a powder, a granule, a mist, an aerosol, a foam, a paste, a dip, a vapor, a paint, and the like, and combinations thereof. In some embodiments of the invention, when the inducer compound is provided in the form of a vapor, the concentration of the inducer compound can be, for example, in a concentration of about 95% to about 100% (v/v). Thus, for example, the inducer compound, provided in a concentration of about 95% to about 100% (v/v), can be placed in proximity to the plant (e.g., in a container such as a tube, a dish, and the like, or on a cloth, paper, beads, and the like, that is soaked in the inducer compound), thereby exposing the plant to a vapor comprising the inducer compound. In some embodiments of the present invention, the inducer compound is provided in more than one form. Thus, for example, the inducer compound can be provided as a foliar spray and as a root drench. The concentration of the inducer compound when applied in more than one form can be the same or can be different in the different forms provided. Thus, for example, a foliar spray and a root drench can be provided at the same and/or a different concentration than one another.

As known in the art, in the *A. nidulans* alcohol dehydrogenase system, the chemical inducer compounds described above act directly on AlcR. AlcR (i.e., AlcR transcription factor) is a transactive regulatory protein that once induced by chemical compounds then induces the expression of the alcohol dehydrogenase system of *A. nidulans*. Upon induction, the Alc R transcription factor binds to the binding sites in the AlcA promoter and other promoters of the *A. nidulans* alcohol dehydrogenas system, thereby inducing the alcohol dehydrogenase system of *A. nidulans*. In representative embodiments of the present invention, when chemically inducible expression of a nucleotide sequence of interest in a plant is desired, AlcR can be used in combination with nucleotide sequences of the invention (i.e., the inverted repeats, (e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:10, in any order, in any orientation, and/or in any combination)). Thus, in some embodiments, Alc R operably associated with a promoter can be used with the methods and compositions of this invention. Accordingly, in some embodiments, a construct comprising AlcR operably associated with a promoter can be used in combination with a construct comprising a chemically inducible promoter of the invention (e.g., nucleotide sequences of the invention in operable association with a promoter/minimal promoter)) as described herein. Any tissue specific/tissue preferable or constitutive promoter can be used with AlcR, thus conferring tissue-specific/preferable or constitutive inducibility, respectively, on the gene of interest that is operably linked to a promoter that is operably linked to the sequences of the invention (e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:10, in any order, in any orientation, and/or in any combination).

For purposes of the invention, the regulatory regions of the nucleic acid molecules of this invention (i.e., promoters, transcriptional regulatory regions, and translational termination regions) can be native/analogous/endogenous to the plant, plant part and/or plant cell and/or the regulatory regions can be native/analogous to the other regulatory regions. Alternatively, the regulatory regions may be heterologous to the plant (and/or plant part and/or plant cell) and/or to each other (i.e., the regulatory regions). Thus, for example, a promoter can be heterologous when it is operably linked to a polynucleotide from a species different from the species from which the polynucleotide was derived. Alternatively, a promoter can also be heterologous to a selected nucleotide sequence if the promoter is from the same/ analogous species from which the polynucleotide is derived, but one or both (i.e., promoter and/or polynucleotide) are modified from their original form and/or genomic locus, or the promoter is not the native promoter for the operably linked polynucleotide.

As described herein, the present invention is directed to methods and compositions for making a promoter inducible or making a promoter having increased inducibility and/or increased sensitivity using compounds that induce the expression of the alcohol dehydrogenase system of *A. nidulans*. However, as discussed herein, the choice of promoters useable with the present invention can be made among many different types of promoters. Thus, the choice of promoter depends upon several factors, including, but not limited to, cell- or tissue-specific expression, desired expression level, efficiency, inducibility and/or selectability. For example, where expression in a specific tissue or organ is desired in addition to inducibility, a tissue-specific promoter can be used (e.g., a root specific promoter). In contrast, where expression in response to a stimulus is desired in addition to inducibility via chemical compounds that induce the expression of the alcohol dehydrogenase system of *A. nidulans*, a promoter inducible by other stimuli or chemicals can be used. Where continuous expression is desired throughout the cells of a plant in addition to inducibility via the chemicals/ compounds of the present invention that induce expression of the alcohol dehydrogenase system of *A. nidulans*, a constitutive promoter can be chosen. In particular embodiments of this invention, a promoter that can be made inducible (or can be made to have increased inducibility and/or increased sensitivity as compared to the native promoter in response to the inducer compounds) by the methods and compositions of the present invention is a minimal promoter. Thus, in further aspects of the invention, whether the nucleotide sequence of interest is expressed in a constitutive manner or in a tissue specific manner is determined by the promoter used with AlcR, and the promoter that is operably linked to the nucleotide sequences of the invention (e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:10, in any order, in any orientation, and/or in any combination)) and to the nucleotide sequence of interest is a minimal promoter.

Non-limiting examples of constitutive promoters include cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci. USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

Some non-limiting examples of tissue-specific promoters useable with the present invention include those encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Thus, the promoters associated with these tissue-specific nucleic acids can be used in the present invention.

Additional examples of tissue-specific promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiol-*

*ogy*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136). Other useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the present invention include but are not limited to the S-E9 small subunit RuBP carboxylase promoter and the Kunitz trypsin inhibitor gene promoter (Kti3).

In some instances, inducible promoters that are not inducible by the same compounds that induce expression of the alcohol dehydrogenase system of *A. nidulans* are useable with the present invention. Examples of inducible promoters useable with the present invention include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters. Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421) the benzene sulphonamide-inducible promoters (U.S. Pat. No. 5,364,780) and the glutathione S-transferase promoters. Likewise, one can use any appropriate inducible promoter described in Gatz (1996) *Current Opinion Biotechnol.* 7:168-172 and Gatz (1997) *Annu. Rev. Plant Physiol. Plant Mol. Biol.* 48:89-108.

The present invention further encompasses plant cells, plant parts and plants in accordance with the embodiments of this invention. Thus, in some embodiments, the present invention provides a transformed plant cell, plant part and/or plant comprising a nucleic acid molecule, a nucleic acid construct, a nucleotide sequence, a promoter, and/or a composition of this invention.

As used herein, "plant" means any plant and thus includes, for example, angiosperms (monocots and dicots), gymnosperms, bryophytes, ferns and/or fern allies. Non-limiting examples of monocot plants of the present invention include sugar cane, corn, barley, rye, oats, wheat, rice, flax, millet, sorghum, grasses, banana, onion, asparagus, lily, coconut, and the like.

In some embodiments, the monocot plants of the invention include plants of the genus *Saccharum* (i.e., sugar cane, energy cane) and hybrids thereof, including hybrids between plants of the genus *Saccharum* and those of related genera, such as *Miscanthus, Erianthus, Sorghum* and others. As used herein, "sugar cane" and "*Saccharum* spp." mean any of six to thirty-seven species (depending on taxonomic interpretation) of tall perennial grasses of the genus *Saccharum*. In particular, the plant can be *Saccharum aegyptiacum, Saccharum esculentum, Saccharum arenicol, Saccharum arundinaceum, Saccharum barberi, Saccharum bengalense, Saccharum biflorum, Saccharum chinense, Saccharum ciliare, Saccharum cylindricum, Saccharum edule, Saccharum elephantinum, Saccharum exaltatum, Saccharum fallax, Saccharum fallax, Saccharum floridulum, Saccharum giganteum, Saccharum hybridum, Saccharum japonicum, Saccharum koenigii, Saccharum laguroides, Saccharum munja, Saccharum narenga, Saccharum officinale, Saccharum officinarum, Saccharum paniceum, Saccharum pophyrocoma, Saccharum purpuratum, Saccharum ravennae, Saccharum robustum, Saccharum roseum, Saccharum sanguineum, Saccharum sara, Saccharum sinense, Saccharum spontaneum, Saccharum tinctorium, Saccharum versicolor, Saccharum violaceum, Saccharum violaceum*, and any of the interspecific hybrids and commercial varieties thereof.

Further non-limiting examples of plants of the present invention include soybean, beans in general, *Brassica* spp., clover, cocoa, coffee, cotton, peanut, rape/canola, safflower, sugar beet, sunflower, sweet potato, tea, vegetables including but not limited to broccoli, brussel sprouts, cabbage, carrot, cassava, cauliflower, cucurbits, lentils, lettuce, pea, peppers, potato, radish and tomato, fruits including, but not limited to, apples, pears, peaches, apricots and citrus, avocado, pineapple and walnuts; and flowers including, but not limited to, carnations, orchids, roses, and any combination thereof.

Definitions

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, activity, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising." Thus, the term "consists essentially of" (and grammatical variants), as applied to a polynucleotide sequence of this invention, means a polynucleotide that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together.

As used herein, the term "plant part" includes but is not limited to embryos, pollen, ovules, seeds, leaves, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein, the terms "fragment" or "portion" when used in reference to a nucleic acid molecule or nucleotide sequence will be understood to mean a nucleic acid molecule or nucleotide sequence of reduced length relative to a reference nucleic acid molecule or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent.

An "isolated" nucleic acid molecule or nucleotide sequence or nucleic acid construct or double stranded RNA molecule of the present invention is generally free of nucleotide sequences that flank the nucleic acid of interest in the genomic DNA of the organism from which the nucleic acid was derived (such as coding sequences present at the 5' or 3' ends). However, the nucleic acid molecule of this invention can include some additional bases or moieties that do not deleteriously or materially affect the basic structural and/or functional characteristics of the nucleic acid molecule.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

Accordingly, "isolated" refers to a nucleic acid molecule, nucleotide sequence, polypeptide, peptide or fragment that is altered "by the hand of man" from the natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated," as the term is employed herein. For example, with respect to polynucleotides, the term isolated means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "complementary" polynucleotides are those that are capable of hybridizing via base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely or fully complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules either along the full length of the molecules or along a portion or region of the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least at about 50%, 60%, 70%, 80% or 90% of their nucleotides. In some embodiments, the two nucleic acid sequences can be complementary at least at about 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, and/or under the control of different regulatory sequences than that found in the native state of the nucleic acid molecule.

As used herein, the terms "transformed" and "transgenic" refer to any plant, plant cell, callus, plant tissue, or plant part that contains all or part of at least one recombinant (e.g, heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transgene" as used herein, refers to any nucleotide sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

Accordingly, the present invention further provides nucleotide sequences having significant sequence identity to the nucleotide sequences of the present invention. Significant sequence similarity or identity means at least 70%, 75%, 80%, 81%, 82%, 83%, 84%, 85%, 86%, 87%, 88%, 89%, 90%, 91%, 92%, 93%, 94%, 96%, 97%, 98%, 99% and/or 100% similarity or identity with another nucleotide sequence.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and/or plastid genome, and therefore includes integration of the nucleic acid into, for example, the chloroplast genome. Stable transformation as used herein can also refer to a nucleic acid molecule that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

Procedures for transforming plants are well known and routine in the art and are described throughout the literature. Non-limiting examples of methods for transformation of plants include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed, transgenic plants, plant cells and/or plant tissue culture are routine in the art and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, the respective nucleotide sequences can be assembled as part of a single nucleic acid construct/molecule, or as separate nucleic acid constructs/molecules, and can be located on the same or different nucleic acid constructs/molecules. Accordingly, the nucleotide sequences can be introduced into the cell of interest in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette. A plant expression cassette can contain regulatory sequences (in addition to SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10) that drive gene expression in plant cells that are operably linked so that each sequence can fulfill its function, for example, termination of transcription by polyadenylation signals. Exemplary polyadenylation signals can be those originating from *Agrobacterium tumefaciens* t-DNA such as the gene known as octopine synthase of the Ti-plasmid pTiACH5 (Gielen et al. *EMBO J.* 3:835 (1984)) or functional equivalents thereof, but also all other terminators functionally active in plants are suitable. A plant expression cassette of this invention can also contain other operably linked sequences like translational enhancers such as the overdrive-sequence containing the 5'-untranslated leader sequence from tobacco mosaic virus enhancing the polypeptide per RNA ratio (Gallie et al. *Nucl. Acids Research* 15:8693-8711 (1987)).

Thus, some embodiments of the invention are directed to expression cassettes designed to express the nucleotide sequences and nucleic acid molecules of the present invention. As used herein, "expression cassette" means a nucleic acid molecule having at least a control sequence operably linked to a nucleotide sequence of interest. In this manner, for example, plant promoters in operable interaction or associate with the nucleotide sequences to be expressed are provided in expression cassettes for expression in a plant, plant part and/or plant cell.

In addition to the promoters operably linked to the nucleotide sequences of the present invention (e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:10) described above, the expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences and polyadenylation signal sequences.

Thus, for example, the AlcR transcription factor is a regulatory sequence that can be used in combination with the nucleic acid molecules/nucleotide sequences of the invention when inducible expression is desired in a plant. AlcR is a transactive regulatory protein that undergoes a conformational change allowing it to bind to cognate binding sites in the promoters of *A. nidulans* alcohol dehydrogenase genes, upon binding any chemical compound that can induce the expression of the alcohol dehydrogenase system of *A. nidulans*. Thus, when used with the methods and compositions of the present invention, upon binding such compounds, the Alc R protein binds to the nucleotide sequences of the invention (i.e., the inverted repeats, (e.g., SEQ ID NO:1, SEQ ID NO:3, SEQ ID NO:4, SEQ ID NO:5, SEQ ID NO:6, SEQ ID NO:7, SEQ ID NO:8, SEQ ID NO:10)), resulting in their induction and thereby inducing the promoter that is operably linked to the nucleotide sequences of the invention. In some embodiments of the invention, the nucleotide sequence encoding the AlcR transcription factor is operably associated with a tissue specific or tissue preferable promoter. In other embodiments, the AlcR transcription factor is operably associated with a constitutive promoter. Promoters usable with the AlcR can be any tissue specific or constitutive promoter. Non-limiting examples of such promoters are provided herein.

Thus, in some embodiments, when used in conjunction with the nucleotide sequences of the present invention, AlcR operably associated with a constitutive promoter enables chemically inducible expression throughout the plant. In other embodiments, when used in conjunction with the nucleotide sequences of the present invention, AlcR operably associated with a tissue-specific/tissue preferable promoter enables chemically inducible expression in specific tissues.

Accordingly, in a representative embodiment, a plant can be transformed with a nucleic acid construct comprising AlcR operably associated with a promoter and a construct comprising the nucleotide sequences of the invention (e.g., SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, in any order, in any orientation, and/or in any combination) operably associated with a promoter. In some embodiments, said constructs are comprised in a single nucleic acid molecule. In other embodiments, said constructs are comprised on different nucleic acid molecules.

Thus, in some embodiments of the present invention, a method of making a plant comprising an isolated nucleotide sequence of interest made inducible using the promoters of the present invention (i.e., inducible by chemical compounds that can induce the expression of the alcohol dehydrogenase system of *A. nidulans*) is provided, the method comprising: introducing into the plant (a) a nucleic acid construct comprising a promoter of the present invention (e.g., a promoter operably linked to one or more nucleotide sequences selected from the group consisting of the nucleotide sequence of SEQ ID NO:1, SEQ ID NO:3, SEQ ID NO:4, SEQ ID NO:5, SEQ ID NO:6, SEQ ID NO:7, SEQ ID NO:8, and SEQ ID NO:10, in any combination, in any orientation, and/in any order) operably linked to said isolated nucleotide sequence of interest; and (b) a nucleic acid molecule comprising a promoter operably linked to AlcR, thereby making a plant comprising an isolated nucleotide sequence of interest that is inducible (using chemical compounds that can induce the expression of the alcohol dehydrogenase system of *A. nidulans*). In some embodiments, the nucleic acid molecules of (a) and (b) are on the same construct. In other embodiments, the nucleic acid molecules of (a) and (b) are on different constructs.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

A signal sequence can be operably linked to a nucleic acid molecule of the present invention to direct the nucleic acid molecule into a cellular compartment. In this manner, the expression cassette will comprise a nucleic acid molecule of the present invention operably linked to a nucleotide sequence for the signal sequence. The signal sequence may be operably linked at the N- or C-terminus of the nucleic acid molecule.

As used herein, "operably linked" means that elements of a nucleic acid construct such as an expression cassette are configured so as to perform their usual function. Thus, regulatory or control sequences (e.g., promoters) operably linked to a nucleotide sequence of interest are capable of effecting expression of the nucleotide sequence of interest. Further, control sequences can be regulated by regulatory sequences. For example, the nucleotide sequences of the invention, e.g., SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10, operably linked to a promoter are capable of effecting inducible expression of the promoter, and therefore can effect inducible expression of any nucleotide sequence of interest that is operably linked to the promoter.

The control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. Thus, in some embodiments of the invention, a nucleotide sequence of interest can be operably linked to a nucleic acid molecule of the present invention (e.g., a nucleic acid molecule comprising one or more nucleotide sequences selected from the group consisting of SEQ ID NO:1, SEQ ID NO:3, SEQ ID NO:4, SEQ ID NO:5, SEQ ID NO:6, SEQ ID NO:7, SEQ ID NO:8, and SEQ ID NO:10 that are operably linked to a promoter), thereby allowing the expression of the nucleotide sequence of interest in a plant, plant part and/or plant cell in an inducible manner.

The expression cassette also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

An expression cassette of the present invention also can include nucleotide sequences that encode other desired traits. Such nucleotide sequences can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or composition of this invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

The expression cassette also can include a coding sequence for one or more polypeptides for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Nucleotide sequences conferring resistance/tolerance to an herbicide that inhibits the growing point or meristem, such as an imidazalinone or a sulfonylurea can also be suitable in some embodiments of the invention. Exemplary nucleotide sequences in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the present invention. See, e.g., U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Nucleotide sequences coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable nucleotide sequences include those coding for resistant to herbicides that inhibit photosynthesis, such as a triazine and a benzonitrile (nitrilase) See, U.S. Pat. No. 4,810,648. Additional suitable nucleotide sequences coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are nucleotide sequences conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Insecticidal proteins useful in the invention may be produced in an amount sufficient to control insect pests, i.e., insect controlling amounts. It is recognized that the amount of production of insecticidal protein in a plant necessary to control insects may vary depending upon the cultivar, type of insect, environmental factors and the like. Nucleotide sequences useful for insect or pest resistance include, for example, those that encode toxins identified in *Bacillus* organisms. Nucleotide sequences encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticidal proteins such as Vip1, Vip2 and Vip3). A full list of Bt toxins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In one embodiment, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, a polypeptide useful for the present invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), (3-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Further enzymes which may be used with the present invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the present invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Production of Non-Optimized Constructs and Transformation into Sugar Cane

A ZmUbi-GS construct was constructed comprising the maize ubiquitin promoter (ZmUbi), the GUS reporter gene containing a synthetic intron (GS), and the nopaline synthase (nos) terminator. The GS sequence consists of a 232 bp $1^{st}$ exon, 84 bp synthetic intron, and 1580 bp $2^{nd}$ exon. The GS sequence was amplified from p35S-GS by polymerase chain reaction (PCR) using the forward primer (5'-CCCGGGATCCTAAACCATGGTCCGTCCTGTA-GAAACCC-3') (SEQ ID NO:11) and reverse primer (5'-TCATTGTTTGCCTCCCTGCTG-3') (SEQ ID NO:12) and KAPAHiFi DNA polymerase (Geneworks). The resulting PCR product was cloned into pGEM-T (Promega) and sequence verified. The GS sequence was excised from pGEM-T using SmaI and NotI, treated with T4 DNA polymerase (Promega) to blunt the NotI ends and then ligated into the SmaI site of a pBluescript (pBS) vector containing the maize Ubi1 promoter and nos terminator (ZmUbi-nos/pBS) to generate ZmUbi-GS.

A ZmUbi-AlcR AlcA-GS construct was constructed comprising the AlcR coding sequence and nos under the control of ZmUbi, as well as GS with nos under the control of the AlcA promoter. The AlcR sequence was amplified from 35S-AlcR-AlcA Rep/pUC by PCR using the forward primer (5'-TTACTTCTGCAGCCCTAAACCATGGCAGA-TACGCGCCGACGCCAG-3') (SEQ ID NO:13) and reverse primer (5'-TGTTTGAACGATCCCCTACAAAAAGCTGT-CAACTTTCCCA-3') (SEQ ID NO:14) and KAPAHiFi DNA polymerase. The resulting PCR product was cloned into the SmaI site of ZmUbi-nos/pBS using the Clontech In Fusion® PCR Cloning System to generate ZmUbi-AlcR, and the PCR product was sequence verified. To generate ZmUbi-AlcR AlcA-GS, the AlcA-GS-nos sequence was subcloned from 35S-AlcR AlcA-GS/pUC into ZmUbi-AlcR using HindIII.

The ZmUbi-GS and ZmUbi-AlcR AlcA-GS constructs were transformed into sugar cane using microprojectile bombardment of callus material. To generate the callus, sugar cane (cultivar Q117) "tops" were obtained from The Bureau of Sugarcane Experimental Stations (BSES) LTD Meringa Queensland, Australia. Calli were initiated as described by Franks and Birch (*Australian J. Plant Physiol.* 18: 471-480 (1991)) using $MSC_3$ media consisting of: 4.43 g/L MS basal salts with vitamins (PhytoTechnology Laboratories®, Shawnee Mission, Kans., USA), 500 mg/L casein hydrolysate (Merck), 13.6 µM 2,4-Dichlorophenoxyacetic acid (2,4-D; Phytotechnology laboratories), 100 ml/L young coconut juice ("Cock" brand, Thailand), 3% (w/v) sucrose and 8 g/L agar (Research organics 10020). Petri dishes used for tissue culture media were 90 mm×25 mm high vented type and sealed with micropore surgical tape. Calli were maintained for nine weeks in the dark at 26° C. and subcultured every 14 days.

Microprojectile bombardment of callus was performed according to the method of Bower et al (Molecular Breeding 1996 2: 239-249). For callus transformation, sugar cane calli were transferred from $MSC_3$ media to MSO media (MS C₃ media with the addition of 190 mM sorbitol (Sigma) and 190 mM mannitol (Sigma) and arranged in a 3 cm diameter circle four hours prior to microprojectile bombardment. The plasmid pUKN (ZmUbi driving expression of the neomycin phosphotransferase II gene) was co-bombarded with each of the GS expression constructs to allow for selection of transformed cells using geneticin. For microprojectile bombardment, a 2 µL aliquot of a 1:1 mixture of pUKN (1 µg/4) and the GS expression construct DNA (1 µg/µL) was added to approximately 3 mg of 1 µm gold particles (Biorad). The solution was vortexed briefly and 25 µL of 1M CaCl₂ and 54 of 0.1M spermidine were added simultaneously. The mixture was iced and vortexed for 15 seconds every minute for a total of 5 minutes. The mixture was then allowed to settle on ice for 10 minutes, after which 22 µL of supernatant was removed. The remaining DNA coated gold solution was mixed and 5 µL was used per bombardment. A particle inflow gun (PIG) was used to deliver the DNA to the target tissue. A baffle utilizing stainless steel mesh screen with an aperture of 500 µm was positioned approximately 1.5 cm above the target tissue within the PIG chamber. The microflight distance of the DNA from the tip of the swinny to the leaf explant was 10.5 cm. The PIG chamber was vacuum evacuated to −90 kPa and a 10 ms pulse of helium at 1500 psi was used to accelerate the microprojectiles. The vacuum was released immediately following bombardment and each sample plate was rotated 180 degrees and subjected to a second bombardment.

Following bombardment, the callus remained on MSO media for four hours. The callus was subsequently transferred to MSC₃ medium for 4-6 days before being transferred to selection media consisting of MSC₃ and 50 mg/L G418 (Geneticin; Roche). Following microprojectile bombardment, the callus remained on selection media for four weeks in the dark with fortnightly subculturing after which it was transferred to regeneration medium with selection, consisting of MSC₃ with the 2,4-D replaced by 4.4 µM 6-Benzylaminopurine (BAP; Sigma). The callus was maintained at 27° C., under a 16 hour light, and 8 hour dark cycle with fortnightly subculturing. Individual plants were separated and one plant from each clump of callus was retained. After ten weeks of regeneration with BAP, the plants were transferred to rooting medium with selection (the same as regeneration medium, however BAP is replaced with 10.7 µM α-Naphthalene Acetic Acid (NAA; Sigma). The plants were grown until roots of approximately 1 cm in length had developed after which the plants were transferred to soil for acclimatization in a growth cabinet under the above mentioned lighting and temperature conditions. After approximately six weeks the plants were transferred to soil in 20 cm pots, and grown in the greenhouse.

Example 2

Characterization of Transgenic Plants Containing Non-Optimized Constructs

Plants were verified to contain the ZmUbi-GS and ZmUbi-AlcR AlcA-GS constructs by TaqMan® analysis for the GUS transgene. Approximately 15 week-old transgenic plants were analyzed for ethanol inducible GUS reporter gene expression. Leaf samples consisting of five standard hole punches were taken from the first fully unfurled leaf of transgenic plants just prior to ethanol induction. Ethanol treatment was carried out by using a 10% ethanol root drench and aerial spray until runoff. After treatment, the plants were enclosed using plastic sheeting to maximize their exposure to the ethanolvapor. After ethanol treatment, first unfurled leaf samples were taken at three and six days post treatment. All leaf samples were collected on ice and used for GUS histochemical analysis (Jefferson et al. EMBO J. 1987 6: 3901-3907) within four hours of collection.

Histochemical analysis was carried out by the addition of GUS staining buffer (50 mM NaPO4 pH 7, 0.1% Triton, 0.5 mM potassium ferrocyanide, 0.5 mM potassium ferricyanide, 10 mM EDTA, and 1 mM X-Gluc), vacuum infiltration of the tissue for 45 minutes, and incubation at 37° C. for 48 hours. After 48 hours, the GUS staining buffer was removed and replaced with 100% ethanol to clear the tissue of chlorophyll. Visual inspection of the cleared leaf discs was used to assess GUS expression.

No ethanol inducible gene expression was detected in any of the leaf samples taken from 21 independent transgenic sugar cane plants containing the ethanol switch construct ZmUbi-AlcR AlcA-GS. In the transgenic sugar cane plants containing the ZmUbi-GS positive control construct, leaf samples from six of 13 independent events showed visible GUS staining in both the uninduced and induced leaf samples.

Ten days after the plants had been treated with 10% ethanol, the transgenic plants were retreated with 2% ethanol using both a root drench and aerial spray until runoff. Leaf samples consisting of five standard hole punches were taken at three and five days post treatment for GUS histochemical staining. Again, none of the leaf samples taken from the 21 transgenic sugar cane plants containing the ethanol switch construct ZmUbi-AlcR AlcA-GS showed any detectable GUS staining.

Example 3

Production of Optimized Ethanol Switch Constructs

To create ethanol switch constructs that may be capable of giving reliable ethanol inducible gene expression in sugar cane, the following modifications were made to the original constructs:
  The AlcR and GUS coding sequences were optimized for expression in sugar cane (Geneart optimization)
  A different kozak sequence (gcggccgcc) was placed immediately upstream of the scoAlcR and scoGUS coding sequences.
  The TMVΩ translational enhancer sequence (gtattttacaacaattaccaacaacaacaaacaacaaacaacattacaattactatttacaattaca) (SEQ ID NO:15) was placed immediately upstream of the kozak.
  12 different AlcA promoter variants were created as follows:
  (1) The SC12 construct has an unmodified AlcA promoter sequence identical to the sequence present in ZmUbi-AlcR AlcA-GS. This AlcA promoter sequence is identical to the original AlcA promoter sequence used in plants as reported in Caddick et al. (*Nature Biotechnology* 6: 177-180 (1998)), and consists of the *Aspergillus* AlcA promoter (from −349 to −112 relative to the translational start site and lacking the upstream direct repeat AlcR binding site) fused to the CaMV 35S minimal promoter (−32 to +3 relative to the CaMV 35S transcriptional start site) at the TATA box (the TATA box is identical in the AlcA and CaMV 35S promoters).
  (2) The SC13 construct consists of the *Aspergillus* AlcA promoter sequence (−349 to −112) fused to a longer CaMV 35S minimal promoter element (−73 to +7 relative to the CaMV 35S transcriptional start site).

(3) The SC14 construct consists of an *Aspergillus* AlcA promoter including the upstream direct repeat AlcR binding site (−400 to −112 relative to the translational start site) fused to the original CaMV 35S minimal sequence (−32 to +3).

(4) The SC15 construct consists of an *Aspergillus* AlcA promoter including the upstream direct repeat AlcR binding site (−400 to −112) fused to the longer CaMV 35S minimal sequence (−73 to +7).

(5) The SC17 construct consists of an *Aspergillus* AlcA promoter (−400 to −112) in which the upstream direct repeat AlcR binding site region has been changed from "cgtccgcatcggcatccgcagc" (SEQ ID NO:16) to "tatccgcatgggtatccgcatg" (SEQ ID NO:17) and fused to the longer CaMV 35S minimal sequence.

(6) The SC18 construct consists of five tandem repeats of the inverted repeat AlcR binding site region sequence "atgcatgcggaaccgcacgagg" (SEQ ID NO:3) at the 5' end of the *Aspergillus* AlcA promoter including the upstream direct repeat AlcR binding site fused to the original CaMV 35S minimal sequence.

(7) The SC19 construct consists of five tandem repeats of the inverted repeat AlcR binding site region sequence "atgcatgcggaaccgcacgagg" (SEQ ID NO:3) at the 5' end of the *Aspergillus* AlcA promoter including the upstream direct repeat AlcR binding site fused to the longer CaMV 35S minimal sequence.

(8) The SC20 construct consists of five tandem repeats of the inverted repeat AlcR binding site region sequence "atgcatgcggaaccgcacgagg" (SEQ ID NO:3) (without any additional AlcA promoter sequence) fused to the longer CaMV 35S minimal sequence.

(9) The SC21 construct consists of the *Aspergillus* AlcA promoter including the upstream direct repeat AlcR binding site fused to the original CaMV 35S minimal sequence with the addition of the maize Adh1 intron (Callis et al. *Genes & Dev.* 1:1183-1200 (1987) at the 3' end.

(10) The SC23 construct consists of the native *Aspergillus* AlcA promoter (−400 to −64 relative to the translational start site).

The sequences for the AlcA promoter variants, sugar cane optimized GUS (scoGUS; with TMVΩ and kozak) with nos terminator, sugar cane optimized AlcR (scoAlcR; with TMVΩ and kozak), and the Adh1 intron (with 15 bp of 5' exon and 6 bp of 3' exon) were made synthetically and included restriction enzyme sites at each end for cloning. The scoAlcR was excised using the flanking, engineered HpaI sites and cloned into the SmaI site of ZmUbi-nos/pBS to generate ZmUbi-scoAlcR. ZmUbi-scoAlcR was digested with EcoRV and SpeI, and the ZmUbi-AlcR-nos region was subcloned into the AvrII (blunted using Klenow) and SpeI sites of the binary construct UbinptIINos(S) to generate scoAlcRnptII. The scoGUS gene with nos was subcloned into pBluescript using PstI and SacII to generate scoGUS/pBS.

All of the AlcA promoter variants were subsequently cloned into scoGUS/pBS using HindIII and PstI. For constructs SC21 and SC22, the Adh1 intron was cloned into the PstI site located between the AlcA promoter and TMVΩ. To generate the final ethanol switch constructs (SC12, SC13, and SC16-20), the AlcA promoter variant, scoGUS, and nos sequences were subcloned into scoAlcRnptII using HindIII and AscI. The final ethanol switch constructs (SC14, SC15, and SC21-23) were made by subcloning the AlcA promoter variant, scoGUS, and nos sequences into scoAlcRnptII using AscI alone.

An optimized, constitutive ZmUbi-scoGUS expression construct was generated as follows: ZmUbi was PCR amplified (adding a HindIII site at the 5' end and a PstI site at the 3' end), cloned into pGEM-T, and sequence verified. ZmUbi was subsequently subcloned into scoGUS/pBS using HindIII and PstI to generate ZmUbi-scoGUS. The ZmUbi-scoGUS and nos sequence was subcloned into the binary construct UbinptIINos(S) using HindIII and AscI.

The binary constructs were transferred into *Agrobacterium* strain AGL1 using a standard heat shock transformation method. *Agrobacterium* containing each of the binary constructs were used to transform sugar cane using following methods (see. Example 4).

Example 4

*Agrobacterium*-Mediated Transformation of Sugar Cane

Plant Source and Material:

Leaf whorl material from field grown sugar cane plants was collected and initiated on EM3 medium (see below). Transverse sections (approximately 20) of immature leaf whorl between 1-3 mm in thickness were taken from just above the meristem and placed in the top-up orientation. Cultures were maintained in the dark at 25° C. for 28 to 42 days. Callus utilized for transformation was within 4-10 days of the last subculture. Callus was selected on morphological characteristics such as compact structure and yellow color. Yellow embryogenic calli were selected wherever possible, as they provided good regeneration, consistent transformation, and fragmented in small clusters (2-4 mm).

Infection and Co-Cultivation:

Callus tissue was heat shocked at 45° C. for 5 minutes by adding 50 ml of pre-warmed ½ strength MS medium (without sucrose) and then maintaining the callus in a water bath at 45° C. MS medium was then drained from the callus tissue, and 25 ml of the *Agrobacterium* inoculation suspension was added to each vessel and mixed gently. The callus/*Agrobacterium* mixture was vacuum-infiltrated by placing it into a vacuum chamber for 10 minutes at −27.5 mmHg of vacuum. The callus/*Agrobacterium* mixture was then rested for 5-10 minutes in the dark.

The *Agrobacterium* inoculation suspension was then drained from the callus, and the remaining callus culture was blotted dry to remove excess *Agrobacterium* inoculation suspension. Plant tissues were blotted on filter paper such as Whatman Grade 1 paper, until the *Agrobacterium* inoculation suspension was substantially removed. The callus was then transferred for co-cultivation to 90×25-mm petri dishes containing no co-culture medium or containing dry filter papers or filter papers wet with sterile water, and sealed with NESCOFILM®, MICROPORE™ tape (3M; Minneapolis, Minn.) or similar material. The dishes were incubated in the dark at 22° C. for 2-3 days.

Post-Transformation:

After co-cultivation, the callus tissue was transferred to MS 1 medium (see below) containing with 200 mg/L of timentin ("resting" medium) and kept in the dark at 25° C. for 4 days. The first selection step was made in MS 2 medium (see below) containing 50 mg/L of geneticin and 200 mg/L of timentin for 14-15 days in the dark at 25° C.

Regeneration and Rooting:

Regeneration was conducted on MS 3 medium (see below) supplemented with 50 mg/L of geneticin and 200 mg/L of timentin at 25° C. in 16 hr light. Gradual increases in light intensity were required. For the first week, the culture was left on a laboratory bench under normal room lighting, and for the next 3 weeks, the culture was grown at moderate light intensity.

Shoot formation was seen between 2-4 weeks. When the first leaves appeared, the shoots were transferred to MS 4 medium (see below) until the plants grew to 4-5 cm in height.

Transformed plants were initially moved from tissue culture and placed in seedling trays containing soil and incubated in a growth chamber. Plants were initially characterized for ethanol inducible GUS expression at 4-7 weeks of age. At approximately eight weeks of age, the plants were moved to 20 cm diameter pots and maintained in a greenhouse. At approximately seven months of age, plants were transferred into 30 cm pots until maturity.

Media:

The components within the media referred to above are as follows.

EM3:

MS salts and vitamins; 0.5 g/L casein hydrolysate; 100 ml/L coconut water; 20 g/L sucrose and 3 mg/l 2,4-D.

LB Basic:

10 g/L NaCl; 5 g/L yeast extract; and 10 g/L tryptone.

LB Solid:

LB basic with 15 g/L of agar.

AB:

The following salts were autoclaved and added: 2 g/L $(NH_4)_2SO_4$; 6 g/L $Na_2HPO_4$; 3 g/L $KH_2PO_4$; and 3 g/L NaCl. The following compounds were filter sterilized: 0.1 mM $CaCl_2$; 1.0 mM $MgCl_2$; 0.003 mM $FeCl_3$; and 5 g/L glucose.

MS Basic:

MS medium salts and vitamins, with 25 g/L sucrose.

MS 1:

MS basic supplemented with 3.0 mg/L 2,4-D and 200 mg/L Timentin.

MS 2:

MS basic supplemented with 3.0 mg/L 2,4-D and 50 mg/L Geneticin and 200 mg/L Timentin.

MS 3:

MS basic supplemented with 40 ml of coconut water filter sterilized and 1.0-2.0 mg/L BAP (cultivar dependent, thus not required for all cultivars) and 50 mg/L Geneticin and 200 mg/L Timentin.

MS 4:

MS basic supplemented with 1.0 g/L charcoal and 1.0 mg IBA (indole-3-butyric acid, not required for all cultivars and 50 mg/L Geneticin.

CoCult:

Media co-cultivation media as described for banana in Khanna et al. *Molecular Breeding* 14(3): 239-252 (2004).

Example 5

Characterization of Transgenic Plants Containing Optimized Constructs

Plants were screened for the presence of the nptII, scoAlcR, and scoGUS genes using TaqMan® analysis. Plants that contained at least one copy of each gene of interest were subsequently characterized for ethanol inducible expression using GUS histochemical staining.

After the transgenic sugar cane plants had been in soil for 4-7 weeks, a leaf sample of approximately 3 cm in length was taken from each plant just prior to ethanol treatment and analyzed for GUS expression by histochemical staining as described above. After sampling, the plants were treated with 2% ethanol using a daily root drench and aerial spray for four days. At five days post treatment, a leaf sample of approximately 3 cm in length was taken from each plant and analyzed for GUS expression by histochemical staining.

Prior to ethanol treatment, only a small number of the ethanol switch plants showed detectable GUS expression while three out of seven ZmUbi-scoGUS plants were found to be GUS positive (Table 1).

Following the 2% ethanol treatment, GUS expression was detected for 11 of the 12 optimized ethanol switch constructs with between 6% and 83% of the plants containing these constructs showing detectable GUS expression (Table 1). Visual inspection of the intensity of staining suggested that constructs SC15, SC18, SC19, SC20, and SC22 gave the highest ethanol inducible expression.

TABLE 1

Results from the histochemical GUS staining of transgenic sugar cane plants containing the different ethanol switch constructs in response to the continuous 2% ethanol treatment.

| Construct | Total Plants (Taqman Positive) | GUS Expression Uninduced | Induced | % Induced |
|---|---|---|---|---|
| SC12 | 12 | 0 | 2 | 17% |
| SC13 | 30 | 0 | 6 | 20% |
| SC14 | 17 | 0 | 1 | 6% |
| SC15 | 16 | 0 | 8 | 50% |
| SC16 | 12 | 1 | 10 | 83% |
| SC17 | 20 | 0 | 4 | 20% |
| SC18 | 10 | 0 | 8 | 80% |
| SC19 | 27 | 0 | 12 | 44% |
| SC20 | 32 | 0 | 12 | 38% |
| SC21 | 6 | 1 | 0 | 0% |
| SC22 | 30 | 2 | 3 | 10% |
| SC23 | 18 | 0 | 10 | 56% |
| pUbi-scoGUS | 7 | 3 | 3 | NA |

An independent group of transgenic sugar cane plants were subsequently analyzed for ethanol inducible expression using a less robust ethanol treatment. After these transgenic plants had been in soil for six weeks, a leaf sample of approximately 3 cm in length was taken from each plant just prior to ethanol treatment and analyzed for GUS expression by histochemical staining. After sampling, the plants were treated with 1% ethanol using a single root drench (800 ml/seedling tray) and aerial spray until runoff. At five days post treatment, a leaf sample of approximately 3 cm in length was taken from each plant and analyzed for GUS expression by histochemical staining.

Prior to ethanol treatment, leaky GUS expression was visible in a subset of the plants for some of the various constructs (Table 2). Following the 1% ethanol treatment, GUS expression was detected for six of the 12 optimized ethanol switch constructs with between 4% and 65% of the plants containing these constructs showing detectable GUS expression (Table 2). Plants containing constructs SC18, SC19 and SC20 had the highest proportion of inducible plants, and visual inspection of the intensity of staining suggested that these plants also had the highest ethanol inducible expression.

TABLE 2

Results for the histochemical GUS staining of transgenic sugar cane plants containing the different ethanol switch constructs in response to the 1% ethanol treatment.

| Construct | Total Plants (Taqman Positive) | GUS Expression Uninduced | Induced | % Induced |
|---|---|---|---|---|
| SC12 | 13 | 4 | 0 | 0% |
| SC13 | 14 | 0 | 0 | 0% |
| SC14 | 14 | 2 | 0 | 0% |
| SC15 | 51 | 12 | 2 | 4% |
| SC16 | 7 | 1 | 2 | 29% |
| SC17 | 20 | 0 | 0 | 0% |
| SC18 | 34 | 16 | 22 | 65% |
| SC19 | 30 | 2 | 19 | 63% |
| SC20 | 32 | 2 | 13 | 41% |
| SC21 | 38 | 13 | 0 | 0% |
| SC22 | 16 | 0 | 0 | 0% |
| SC23 | 15 | 2 | 1 | 7% |

For the quantitative analysis of ethanol inducible expression in more mature plants, only the single copy plants for each construct were selected and transferred to the greenhouse. When the transgenic sugar cane plants had been in soil for approximately six months they were assessed to verify that there was no residual GUS expression from the previous ethanol treatment that was carried out at 4-7 weeks of age. To do this, a tissue sample was taken from the first fully unfurled leaf of each plant and analyzed for GUS expression by histochemical staining. No residual GUS expression from the original ethanol treatment was detected in these transgenic plants.

Subsequently, these plants were reanalyzed for ethanol inducible expression. A tissue sample roughly equivalent to one standard hole punch was taken from the top, middle, and bottom of the first fully unfurled leaf of each plant. These three leaf samples were combined and placed into one well of a 96 well sample block on ice. Each plant was sampled in duplicate from the same first unfurled leaf. Samples were then frozen at −80° C. and freeze dried. After sampling, the plants were treated with 5% ethanol using a single root drench (700 ml/pot) and aerial spray until runoff. At two, four, and seven days post treatment, a tissue sample roughly equivalent to one standard hole punch was taken from the top, middle, and bottom of the same first fully unfurled leaf of each plant. These three leaf samples were combined and placed into one well of a 96 well sample block on ice. Each plant was sampled in duplicate from the same first unfurled leaf at each timepoint. Samples were frozen at −80° C., freeze-dried, and GUS expression was subsequently quantitated by ELISA.

For the GUS ELISA, high-binding 96-well plates (Nunc Maxisorp®) were coated at 4° C. overnight with 2 µg/ml rabbit anti-GUS IgG (Sigma G5545) in 25 mM borate, 75 mM NaCl, pH 8.5 (100 µl/well). Plates were washed three times with 10 mM Tris, pH 8.0 containing 0.05% Tween-20 and 0.2% $NaN_3$. Samples or standards (GUS Type VII-A, Sigma G7646) were added to the plate (100 µl/well), incubated for 1 hr at room temperature with shaking, and washed five times. 100 µl/well of 2 µg/ml HRP-labeled rabbit anti-GUS IgG (Invitrogen A5790 conjugated to HRP) was then added to the plate, incubated for 1 hr at room temperature with shaking, and washed as before. The HRP-conjugated antibody was detected by adding 100 µl/well tetramethylbenzidine (TMB, Sigma T0440) and developing for 30 min at room temperature. The reaction was stopped by the addition of 100 µl/well of 0.1N HCl. The absorbance was measured at 450 nm with 620 as a reference using a microplate reader (Tecan Sunrise™, Research Triangle Park, N.C.). The GUS standard curve uses a 4-parameter curve fit. The curve is plotted linear vs. log with a range from 0 to 320 ng/ml.

Results from the GUS ELISA indicated that there was no detectable GUS expression in any of the transgenic sugar cane plants prior to ethanol treatment. Following ethanol treatment, the highest, most consistent ethanol inducible expression was detected from those plants containing the constructs with multiple copies of the inverted repeat AlcR binding site (SC18, SC19, and SC20; FIG. 1). Little or no ethanol inducible expression was detected in plants containing the other nine constructs. These results indicate that multiple copies of the inverted repeat AlcR binding site can substantially improve ethanol inducible gene expression.

Example 6

Production and Testing of Additional Inducible Promoter Constructs with Varying Numbers of the Inverted Repeat AlcR Binding Site Nucleic acid constructs having one copy or nine copies of the inverted repeat AlcR binding site were generated as follows:

(1) The SC35 construct consists of one copy of the inverted repeat AlcR binding site region sequence "atgcatgcggaaccgcacgagg" (SEQ ID NO:3) (without any additional AlcA promoter sequence) fused to the longer CaMV 35S minimal sequence (−73 to +7 relative to the CaMV 35S transcriptional start site).

(2) The SC36 construct consists of nine tandem repeats of the inverted repeat AlcR binding site region sequence "atgcatgcggaaccgcacgagg" (SEQ ID NO:3) (without any additional AlcA promoter sequence) fused to the longer CaMV 35S minimal sequence.

The SC35 and SC36 promoter sequences were made synthetically and included restriction enzyme sites at each end for cloning. These sequences were cloned into scoGUS/pBS using HindIII and PstI. To generate the final ethanol switch constructs the promoter variant, scoGUS, and nos sequences were subcloned into scoAlcRnptII using HindIII and AscI. The binary SC35 and SC36 constructs were transferred into Agrobacterium strain AGL1 using a standard heat shock transformation method. Agrobacterium containing each of the binary constructs were used to transform sugar cane as described above.

Plants were screened for the presence of the nptII, scoAlcR, and scoGUS genes using TaqMan® analysis. Plants that contained at least one copy of each gene of interest were subsequently characterized for ethanol inducible expression using GUS ELISA as described above. After the transgenic sugar cane plants were in soil for approximately six weeks, a leaf sample of approximately 3 cm in length was taken from the first fully unfurled leaf of each plant just prior to ethanol treatment and placed into one well of a 96 well sample block on ice. Each plant was sampled in duplicate from the same first unfurled leaf. Samples were frozen at −80° C. and freeze dried. After sampling, the plants were treated with 2% ethanol using a single root drench (800 ml/seedling tray) and aerial spray until runoff. At four days post treatment, a leaf sample of approximately 3 cm in length was taken from the same leaf previously sampled, and placed into one well of a 96 well sample block on ice. Each plant was sampled in duplicate from the same first unfurled leaf. Samples were frozen at −80° C., freeze-dried, and GUS expression was subsequently quantitated by ELISA as described above.

Figure 2:
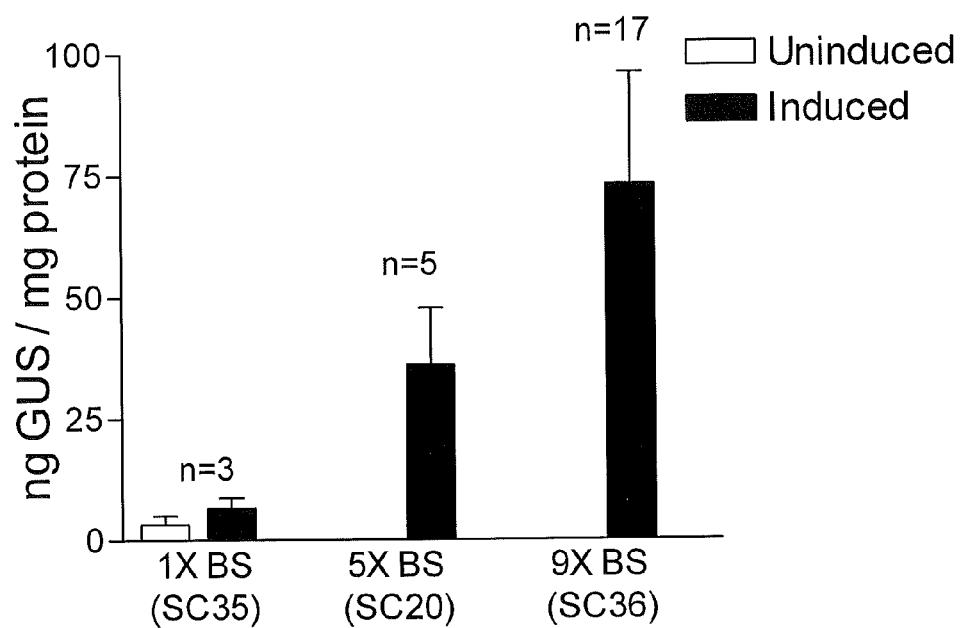
FIG. 2 shows ethanol inducible expression from promoters containing either 1, 5, or 9 copies of the inverted repeat AlcR binding site.

Prior to ethanol treatment, little or no GUS expression was detected in the leaves of the transgenic sugar cane plants (Table 3, FIG. 2). Following ethanol treatment, robust ethanol inducible expression was detected from those plants containing the constructs with either five or nine copies of the inverted repeat AlcR binding site (SC20 and SC36; Table 3 and FIG. 2). Only low levels of ethanol inducible expression were detected from plants containing the construct with one copy of the inverted repeat AlcR binding site (SC35; Table 3 and FIG. 2). Furthermore, a substantially higher percentage of the transgenic plants containing the constructs with multiple inverted repeat AlcR binding sites (SC20 and SC36) showed ethanol inducible expression compared to those plants containing a single copy of the inverted repeat AlcR binding site (SC35; Table 3).

TABLE 3

Ethanol inducible expression from promoters containing either 1, 5, or 9 copies of the inverted repeat AlcR binding site.

| Construct ID | Uninduced Expression (ng GUS/mg protein) | Induced Expression (ng GUS/mg protein) | Plants showing detectable expression (% of TaqMan ® positive plants showing expression) |
|---|---|---|---|
| SC35 | 3.3 ± 1.7 | 6.6 ± 2.3 | 3 (23%) |
| SC20 | 0 | 36.1 ± 11.8 | 5 (100%) |
| SC36 | 0 | 73.2 ± 23.0 | 17 (71%) |

Example 7

Production and Testing of Additional Inducible Promoter Constructs in Sugarcane

To identify the minimal sequence within the inverted repeat AlcR binding site that is necessary for ethanol inducible expression, the following modified inverted repeat AlcR binding sites were generated:

(1) The SC38 construct modifies the inverted repeat AlcR binding site region sequence "atgcatgcggaaccgcacgagg" (SEQ ID NO:3) to "tacgtagcggaaccgctgctcc" (SEQ ID NO:6).

(2) The SC39 construct modifies the inverted repeat AlcR binding site region sequence "atgcatgcggaaccgcacgagg" (SEQ ID NO:3) to "tacgttgcggaaccgcagctcc" (SEQ ID NO:10).

(3) The SC41 construct modifies the inverted repeat AlcR binding site region sequence "atgcatgcggaaccgcacgagg" (SEQ ID NO:3) to "atgcatgcggtgccgcacgagg" (SEQ ID NO:8).

(4) The SC42 construct modifies the inverted repeat AlcR binding site region sequence "atgcatgcggaaccgcacgagg" (SEQ ID NO:3) to "atgcatgcggaatgcaaccgcacgagg" (SEQ ID NO:9).

The above sequences were synthesized as pentamers fused with the long 35S minimal sequence. These modified promoter variants were cloned as described above (Example 5). The binary SC38, SC39, SC41 and SC42 constructs were transferred into Agrobacterium strain AGL1 using a standard heat shock transformation method. Agrobacterium containing each of the binary constructs were used to transform sugar cane as described above. Ethanol inducibility from these promoters was compared to that of construct SC20 using GUS ELISA as described above.

Figure 3:
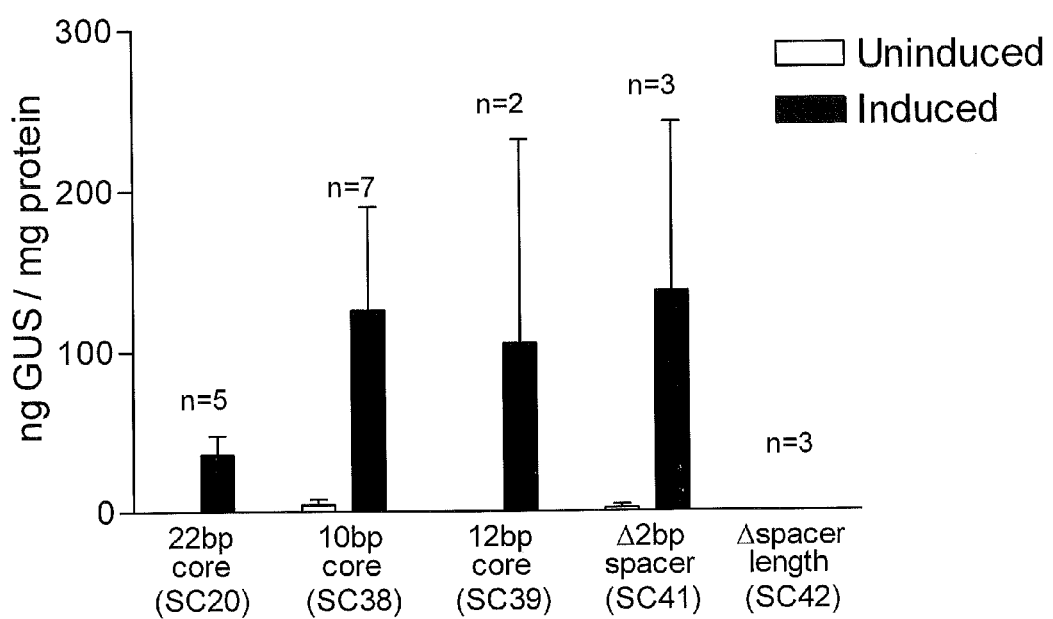
FIG. 3 shows ethanol inducible expression from promoters containing various modified inverted repeat AlcR binding sites.

Prior to ethanol treatment, little or no GUS expression was detected in the leaves of the transgenic sugar cane plants (Table 4, FIG. 3). Following ethanol treatment, robust ethanol inducible expression was detected from those plants containing the constructs with the various point mutations to the inverted repeat AlcR binding site (SC38, SC39, and SC41; Table 4 and FIG. 3). In addition, 100% of the transgenic plants containing these constructs were found to exhibit ethanol inducible expression (Table 4). No ethanol inducible expression was detected from transgenic plants containing the construct that alters the length of the 2 bp spacer between the inverted repeat AlcR binding sites (SC42; Table 4 and FIG. 3). From this data, the sequence of "GCGGnnCCGC" (with n representing any nucleotide) can be defined as a minimal sequence necessary for ethanol inducible expression.

TABLE 4

Ethanol inducible expression from promoters containing various modified inverted repeat AlcR binding sites.

| Construct ID | Uninduced Expression (ng/mg protein) | Induced Expression (ng/mg protein) | Plants showing detectable expression (% of TaqMan ® positive plants showing expression) |
|---|---|---|---|
| SC20 | 0 | 36.1 ± 11.8 | 5/5 (100%) |
| SC38 | 4.4 ± 3.5 | 125.8 ± 64.3 | 7/7 (100%) |
| SC39 | 0 | 105.1 ± 126.8 | 2/2 (100%) |
| SC41 | 2.2 ± 2.2 | 137.3 ± 105.4 | 3/3 (100%) |
| SC42 | 0 | 0 | 0/3 (0%) |

Example 8

Preparation and Testing of a Maize Promoter in Combination with the AlcR "b" Inverted Repeat Binding Sites The minimal maize Adh1 promoter, as described by Walker et al. ((1987) PNAS, 84: 6624-6628), can be tested for its ability to be made inducible using the nucleotide sequence of SEQ ID NO:1, SEQ ID NO:3, SEQ ID NO:4, SEQ ID NO:5, SEQ ID NO:6, SEQ ID NO:7, SEQ ID NO:8, and/or SEQ ID NO:10. The Adh1 nucleotide sequence (SEQ ID NO:18), below, was identified by successive 5' deletions of the Adh1 promoter, and shown to give only background levels of expression.

(SEQ ID NO: 18)
ccacaggcggccaaaccgcaccctccttcccgtcgtttcccatctcttcctcctttagagctaccactatataaatcagggctcattttct cgctcctcacaggctcatctcgctttggatcgattggtttcgtaactggtgaaggactgagggtctcggagtggatgatttgggattctgtt cgaagatttgcggagggggca + 106

The maize Adh1 minimal promoter sequence was fused with five tandem repeats of the inverted repeat AlcR binding site region sequence "atgcatgcggaaccgcacgagg" (SEQ ID NO:3) (replacing the long 35S minimal promoter sequence as described in Example 3, construct SC20). Ethanol inducibility of this promoter (SC37) was compared to that of construct SC20 using GUS ELISA as described above.

Figure 4:
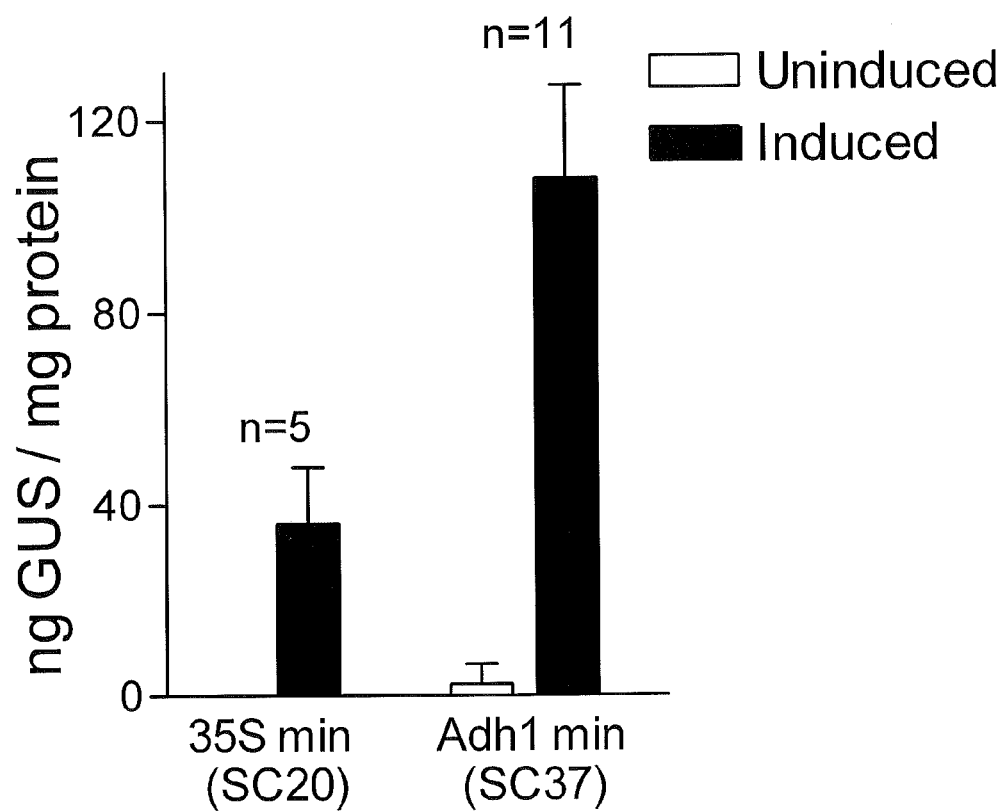
FIG. 4 shows ethanol inducible expression from promoters containing five copies of the inverted repeat AlcR binding sites fused to different minimal promoters.

Prior to ethanol treatment, little or no GUS expression was detected in the leaves of the transgenic sugar cane plants (Table 5 and FIG. 4). Following ethanol treatment, robust ethanol inducible expression was detected from those plants containing the construct with the five copies of the inverted repeat AlcR binding sites fused to the maize Adh1 minimal promoter (Table 5 and FIG. 4).

TABLE 5

Ethanol inducible expression from promoters containing five copies of the inverted repeat AlcR binding sites fused to different minimal promoters.

| Construct ID | Uninduced Expression (ng/mg protein) | Induced Expression (ng/mg protein) | Plants showing detectable expression (% of TaqMan® positive plants showing expression) |
|---|---|---|---|
| SC20 | 0 | 36.1 ± 11.8 | 5/5 (100%) |
| SC37 | 2.5 ± 4.3 | 107.9 ± 19.4 | 11 (69%) |

Example 9

Characterization of Ethanol Inducible Expression in the Vegetative Plantings of the Primary Transgenic Sugar Cane Plants Single-bud setts from stems of selected mature, T0 transgenic plants were planted in soil and maintained in a glasshouse. After the T0V1 transgenic sugar cane plants were in soil for approximately four months (at which time they were comparable in size to the six month old T0 plants describe above), a leaf sample of approximately 3 cm in length was taken from the first fully unfurled leaf of each plant just prior to ethanol treatment and placed into one well of a 96 well sample block on ice. Each plant was sampled in duplicate from the same first unfurled leaf Samples were frozen at −80° C. and freeze dried. After sampling, the T0V1 plants were treated with 5% ethanol using a single root drench (700 ml/pot) and aerial spray until runoff. At four days post treatment, a leaf sample of approximately 3 cm in length was taken from the same leaf previously sampled, and placed into one well of a 96 well sample block on ice. Each plant was sampled in duplicate from the same first unfurled leaf. Samples were frozen at −80° C., freeze-dried, and GUS expression was subsequently quantitated by ELISA as described above.

Figure 5:
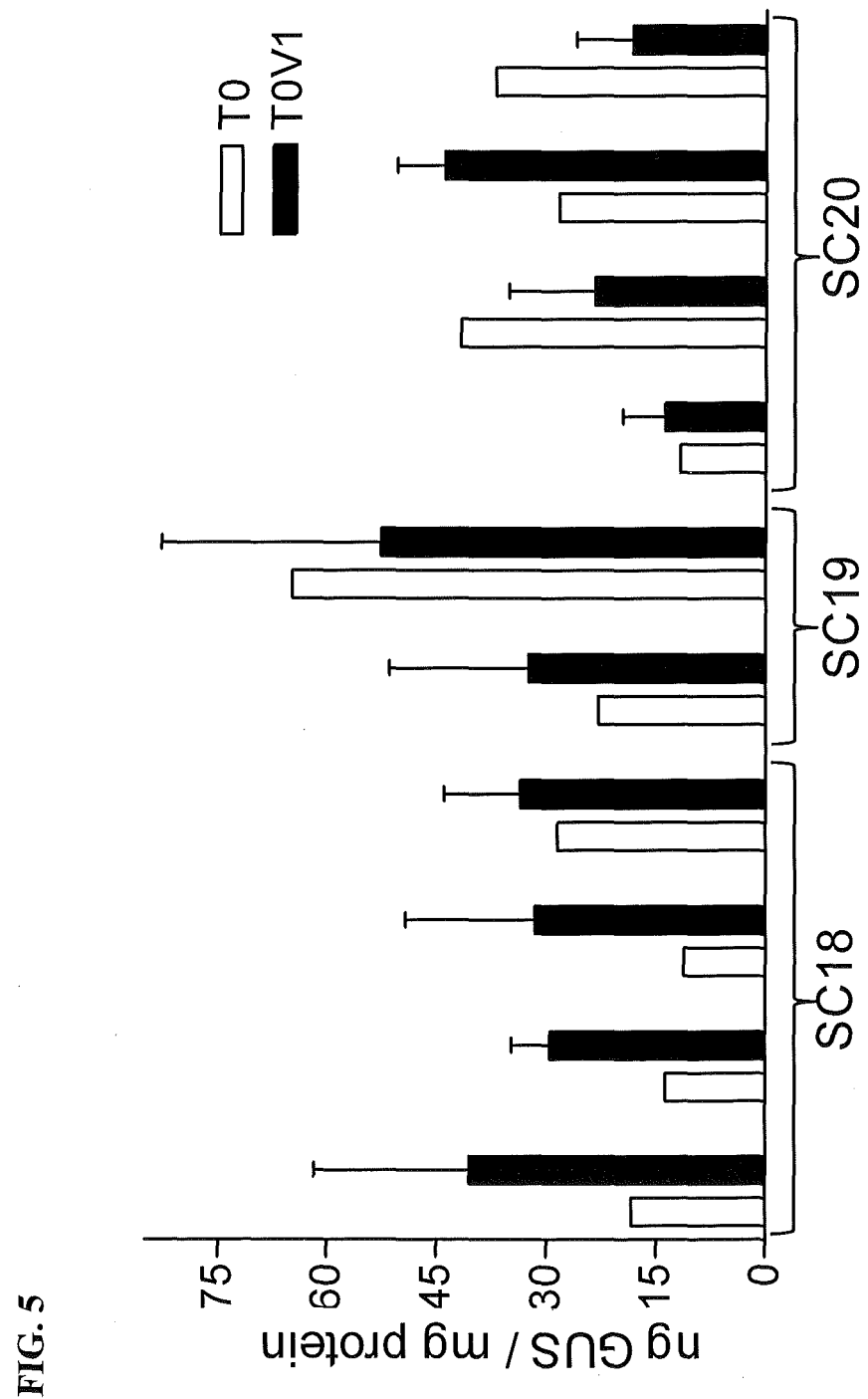
FIG. 5 shows ethanol inducible expression in the T0 and T0V1 transgenic plants.

Prior to ethanol treatment, little or no GUS expression was detected in the leaves of the T0V1 transgenic sugar cane plants (data not shown). Following ethanol treatment, robust ethanol inducible expression was detected for all of the T0V1 transgenic plants (FIG. 5), indicating that ethanol inducibility from these constructs is maintained in the vegetatively-propagated material.

The foregoing is illustrative of the present invention, and is not to be construed as limiting thereof. The invention is defined by the following claims, with equivalents of the claims to be included therein.

What is claimed is:

1. An isolated nucleic acid molecule comprising five to nine nucleotide sequences selected from the group consisting of SEQ ID NO: 3, SEQ ID NO: 4, SEQ ID NO: 5, SEQ ID NO: 6, SEQ ID NO: 7, SEQ ID NO: 8, and SEQ ID NO: 10, wherein the selected nucleotide sequences can be in any combination, in any orientation, and/or in any order, and wherein the five to nine nucleotide sequences are operably linked to a heterologous promoter.

2. The isolated nucleic acid molecule of claim 1, wherein the heterologous promoter is further operably linked to a nucleotide sequence of interest.

3. A method of making a promoter inducible, comprising:
a) constructing a nucleic acid molecule comprising five to nine nucleotide sequences selected from the group consisting of SEQ ID NO: 3, SEQ ID NO: 4, SEQ ID NO: 5, SEQ ID NO: 6, SEQ ID NO: 7, SEQ ID NO: 8, and SEQ ID NO: 10, in any combination, in any orientation, and/or in any order; and
b) operably linking the nucleic acid molecule of (a) with the promoter, wherein the promoter is heterologous to the five to nine nucleotide sequences of the nucleic acid molecule.

4. The method of claim 3, wherein the heterologous promoter is made inducible to a chemical compound selected from the group consisting of a primary alcohol, a primary monoamine, a ketone, a methyl ketone, a hydrolysable ester, an aliphatic aldehyde, and any combination thereof.

5. The method of claim 3, wherein the heterologous promoter is made inducible to a chemical compound selected from the group consisting of ethanol, acetaldehyde, ethyl methyl ketone, acetone, ethylamine, cyclohexanone, butan-2-ol, 3-oxobutyric acid, propan-2-ol, propan-1-ol, butan-2-ol, threonine, and any combination thereof.

6. The method of claim 3, wherein the heterologous promoter that is made inducible is a constitutive promoter, a tissue specific promoter, a developmentally regulated promoter, and/or a chemically inducible promoter that is inducible by compounds that do not induce the expression of the alcohol dehydrogenase system of *Aspergillus nidulans*.

7. The method of claim 3, wherein the heterologous promoter is a minimal promoter.

8. The method of claim 3, wherein the five to nine nucleotide sequences are at the 5' end of the nucleic acid molecule.

9. A method of making the expression of a nucleotide sequence of interest inducible comprising operably linking the heterologous promoter of claim 1 to the nucleotide sequence of interest.

10. A promoter made by the method of claim 3.

11. A plant, plant part or plant cell comprising the isolated nucleic acid molecule of claim 2.

* * * * *

SEQUENCE LISTING

```
<160> NUMBER OF SEQ ID NOS: 18

<210> SEQ ID NO 1
<211> LENGTH: 210
<212> TYPE: DNA
<213> ORGANISM: Artificial
<220> FEATURE:
<223> OTHER INFORMATION: Inducible promoter construct sequence
<220> FEATURE:
<221> NAME/KEY: misc_feature
<222> LOCATION: (1)..(100)
<223> OTHER INFORMATION: n is optionally present and may be a, c, g, or
      t
<220> FEATURE:
<221> NAME/KEY: misc_feature
<222> LOCATION: (105)..(106)
<223> OTHER INFORMATION: n is a, c, g, or t
<220> FEATURE:
<221> NAME/KEY: misc_feature
<222> LOCATION: (111)..(210)
<223> OTHER INFORMATION: n is optionally present and may be a, c, g, or
      t

<400> SEQUENCE: 1
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn gcggnnccgc nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn                                     210
```

```
<210> SEQ ID NO 2
<211> LENGTH: 215
<212> TYPE: DNA
<213> ORGANISM: Artificial
<220> FEATURE:
<223> OTHER INFORMATION: Inducible promoter construct sequence
<220> FEATURE:
<221> NAME/KEY: misc_feature
<222> LOCATION: (1)..(100)
<223> OTHER INFORMATION: n is optionally present and may be a, c, g, or
      t
<220> FEATURE:
<221> NAME/KEY: misc_feature
<222> LOCATION: (105)..(111)
<223> OTHER INFORMATION: n is a, c, g, or t
<220> FEATURE:
<221> NAME/KEY: misc_feature
<222> LOCATION: (116)..(215)
<223> OTHER INFORMATION: n is optionally present and may be a, c, g, or
      t

<400> SEQUENCE: 2
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn gcggnnnnnn nccgcnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnn                                215

<210> SEQ ID NO 3
<211> LENGTH: 22
<212> TYPE: DNA
<213> ORGANISM: Artificial
<220> FEATURE:
<223> OTHER INFORMATION: Inducible promoter construct sequence

<400> SEQUENCE: 3
atgcatgcgg aaccgcacga gg                                               22

<210> SEQ ID NO 4
<211> LENGTH: 22
<212> TYPE: DNA
<213> ORGANISM: Artificial
<220> FEATURE:
<223> OTHER INFORMATION: Inducible promoter construct sequence

<400> SEQUENCE: 4
ggccatgcgg agccgcacgc gt                                               22

<210> SEQ ID NO 5
<211> LENGTH: 22
<212> TYPE: DNA
<213> ORGANISM: Artificial
<220> FEATURE:
<223> OTHER INFORMATION: Inducible promoter construct sequence

<400> SEQUENCE: 5
acaagagcgg ctccgcttga cc                                               22

<210> SEQ ID NO 6
<211> LENGTH: 22
<212> TYPE: DNA
<213> ORGANISM: Artificial
<220> FEATURE:
<223> OTHER INFORMATION: Inducible promoter construct sequence

<400> SEQUENCE: 6
```

```
tacgtagcgg aaccgctgct cc                                              22

<210> SEQ ID NO 7
<211> LENGTH: 22
<212> TYPE: DNA
<213> ORGANISM: Artificial
<220> FEATURE:
<223> OTHER INFORMATION: Inducible promoter construct sequence

<400> SEQUENCE: 7
taccatgcgg aaccgcacgt cc                                              22

<210> SEQ ID NO 8
<211> LENGTH: 22
<212> TYPE: DNA
<213> ORGANISM: Artificial
<220> FEATURE:
<223> OTHER INFORMATION: Inducible promoter construct sequence

<400> SEQUENCE: 8
atgcatgcgg tgccgcacga gg                                              22

<210> SEQ ID NO 9
<211> LENGTH: 27
<212> TYPE: DNA
<213> ORGANISM: Artificial
<220> FEATURE:
<223> OTHER INFORMATION: Inducible promoter construct sequence

<400> SEQUENCE: 9
atgcatgcgg aatgcaaccg cacgagg                                         27

<210> SEQ ID NO 10
<211> LENGTH: 22
<212> TYPE: DNA
<213> ORGANISM: Artificial
<220> FEATURE:
<223> OTHER INFORMATION: Inducible promoter construct sequence

<400> SEQUENCE: 10
tacgttgcgg aaccgcagct cc                                              22

<210> SEQ ID NO 11
<211> LENGTH: 38
<212> TYPE: DNA
<213> ORGANISM: Artificial
<220> FEATURE:
<223> OTHER INFORMATION: PCR primer

<400> SEQUENCE: 11
cccgggatcc taaaccatgg tccgtcctgt agaaaccc                             38

<210> SEQ ID NO 12
<211> LENGTH: 21
<212> TYPE: DNA
<213> ORGANISM: Artificial
<220> FEATURE:
<223> OTHER INFORMATION: PCR primer

<400> SEQUENCE: 12
tcattgtttg cctccctgct g                                               21

<210> SEQ ID NO 13
<211> LENGTH: 45
<212> TYPE: DNA
<213> ORGANISM: Artificial
```

```
<220> FEATURE:
<223> OTHER INFORMATION: PCR primer

<400> SEQUENCE: 13
ttacttctgc agccctaaac catggcagat acgcgccgac gccag            45

<210> SEQ ID NO 14
<211> LENGTH: 40
<212> TYPE: DNA
<213> ORGANISM: Artificial
<220> FEATURE:
<223> OTHER INFORMATION: PCR primer

<400> SEQUENCE: 14
tgtttgaacg atcccctaca aaaagctgtc aactttccca                  40

<210> SEQ ID NO 15
<211> LENGTH: 68
<212> TYPE: DNA
<213> ORGANISM: Tobacco mosaic virus

<400> SEQUENCE: 15
gtatttttac aacaattacc aacaacaaca aacaacaaac aacattacaa ttactattta    60
caattaca                                                             68

<210> SEQ ID NO 16
<211> LENGTH: 22
<212> TYPE: DNA
<213> ORGANISM: Aspergillus nidulans

<400> SEQUENCE: 16
cgtccgcatc ggcatccgca gc                                     22

<210> SEQ ID NO 17
<211> LENGTH: 22
<212> TYPE: DNA
<213> ORGANISM: Artificial
<220> FEATURE:
<223> OTHER INFORMATION: AlcA promoter sequence modification

<400> SEQUENCE: 17
tatccgcatg ggtatccgca tg                                     22

<210> SEQ ID NO 18
<211> LENGTH: 205
<212> TYPE: DNA
<213> ORGANISM: Artificial
<220> FEATURE:
<223> OTHER INFORMATION: Minimal maize Adh1 promoter sequence

<400> SEQUENCE: 18
ccacaggcgg ccaaaccgca ccctccttcc cgtcgtttcc catctcttcc tcctttagag    60
ctaccactat ataaatcagg gctcattttc tcgctcctca caggctcatc tcgctttgga   120
tcgattggtt tcgtaactgg tgaaggactg agggtctcgg agtggatgat ttgggattct   180
gttcgaagat ttgcggaggg gggca                                        205
```